United States Patent
Abbasi et al.

(10) Patent No.: US 11,446,163 B1
(45) Date of Patent: Sep. 20, 2022

(54) CANNULATED ENDPLATE PLUNGER

(71) Applicant: Advance Research System, LLC, Edina, MN (US)

(72) Inventors: Hamid R. Abbasi, Edina, MN (US); Stuart J. Olstad, Plymouth, MN (US)

(73) Assignee: Advanced Research Systems, LLC, Edina, MN (US)

( * ) Notice: Subject to any disclaimer, the term of this patent is extended or adjusted under 35 U.S.C. 154(b) by 51 days.

(21) Appl. No.: 16/839,167

(22) Filed: Apr. 3, 2020

Related U.S. Application Data

(60) Provisional application No. 62/902,506, filed on Sep. 19, 2019, provisional application No. 62/829,690, filed on Apr. 5, 2019.

(51) Int. Cl.
*A61F 2/46* (2006.01)
*A61F 2/44* (2006.01)
*A61F 2/30* (2006.01)

(52) U.S. Cl.
CPC ............ *A61F 2/4611* (2013.01); *A61F 2/447* (2013.01); *A61F 2002/30112* (2013.01); *A61F 2002/4627* (2013.01)

(58) Field of Classification Search
CPC .................... A61F 2/4611; A61F 2/447; A61F 2002/4495; A61F 2220/0075; A61F 2220/066; A61F 2002/30112; A61F 2002/4627; A61B 17/0401; A61B 2017/0409; A61B 2017/0414; A61B 2017/042
See application file for complete search history.

(56) References Cited

U.S. PATENT DOCUMENTS

| | | |
|---|---|---|
| 5,755,732 A | 5/1998 | Green et al. |
| 6,350,284 B1 | 2/2002 | Törmälä et al. |
| 6,746,451 B2 | 6/2004 | Middleton et al. |
| 7,223,289 B2 | 5/2007 | Trieu et al. |
| 7,500,977 B2 | 3/2009 | Assell et al. |
| 7,655,015 B2 | 2/2010 | Goldfarb et al. |
| 9,662,123 B2 | 5/2017 | Tally et al. |
| 2015/0127021 A1* | 5/2015 | Harris .............. A61B 17/00234 606/143 |

* cited by examiner

*Primary Examiner* — Zade Coley
*Assistant Examiner* — Diana Jones
(74) *Attorney, Agent, or Firm* — Christensen, Fonder, Dardi & Herbert PLLC; Stuart J. Olstad

(57) ABSTRACT

An endplate plunger for implanting a growth-promoting tether between opposed adjacent vertebrae. The endplate plunger includes resilient arm assemblies that store potential energy when the endplate plunger is in a retracted configuration. In transitioning from the retracted configuration to a deployed configuration, the potential energy is released in a burst of kinetic energy, causing tip portions at the distal ends of the resilient arm assemblies to be thrust into the adjacent vertebrae. In some embodiments, each tip portion forms a cleft in the respective vertebral endplate and deposits the tether therein. The tether is thereby anchored directly in the clefts, without need for separately formed anchors. In some embodiments, devices and methods are disclosed to route the tether through an implanted spinal implant.

20 Claims, 13 Drawing Sheets

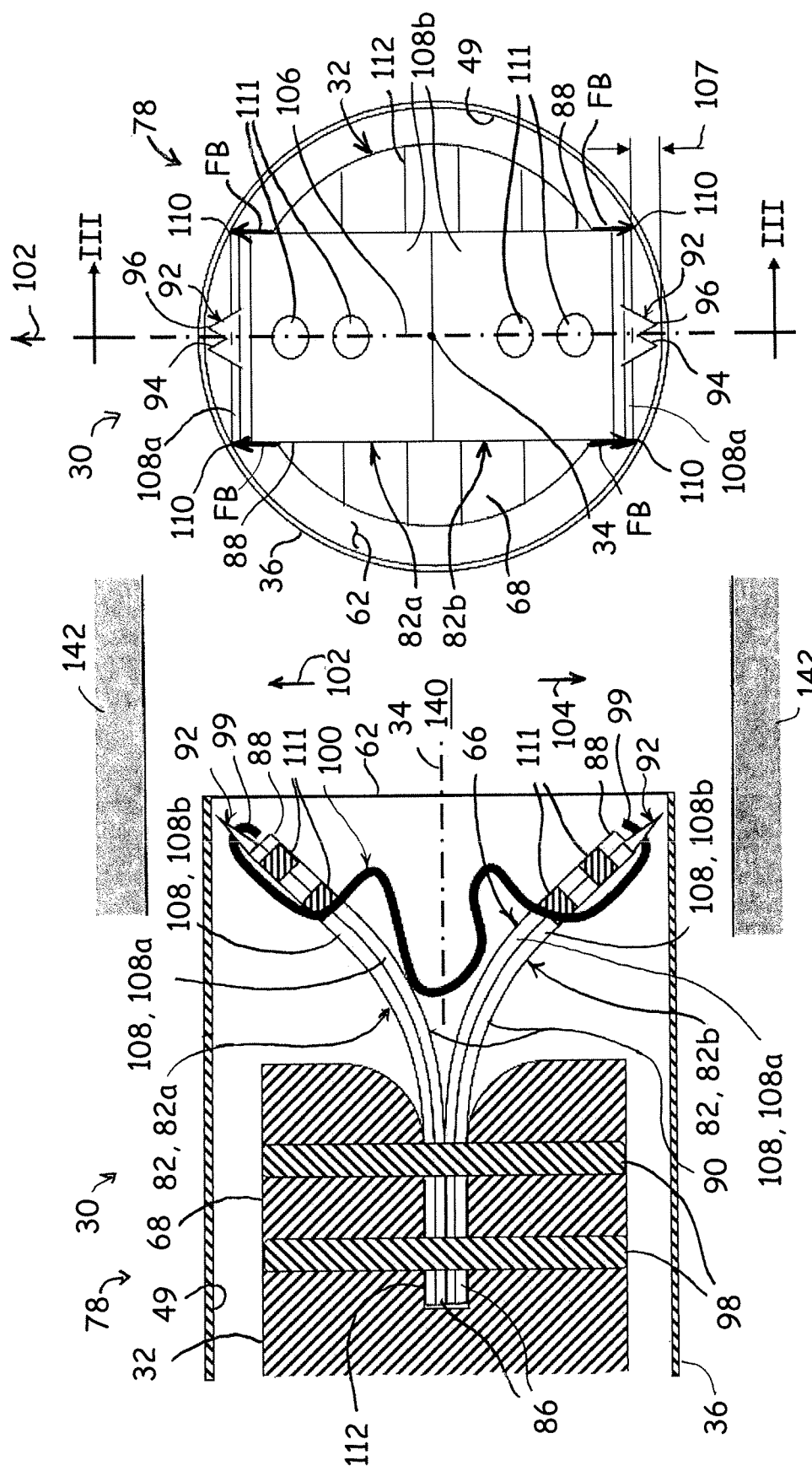

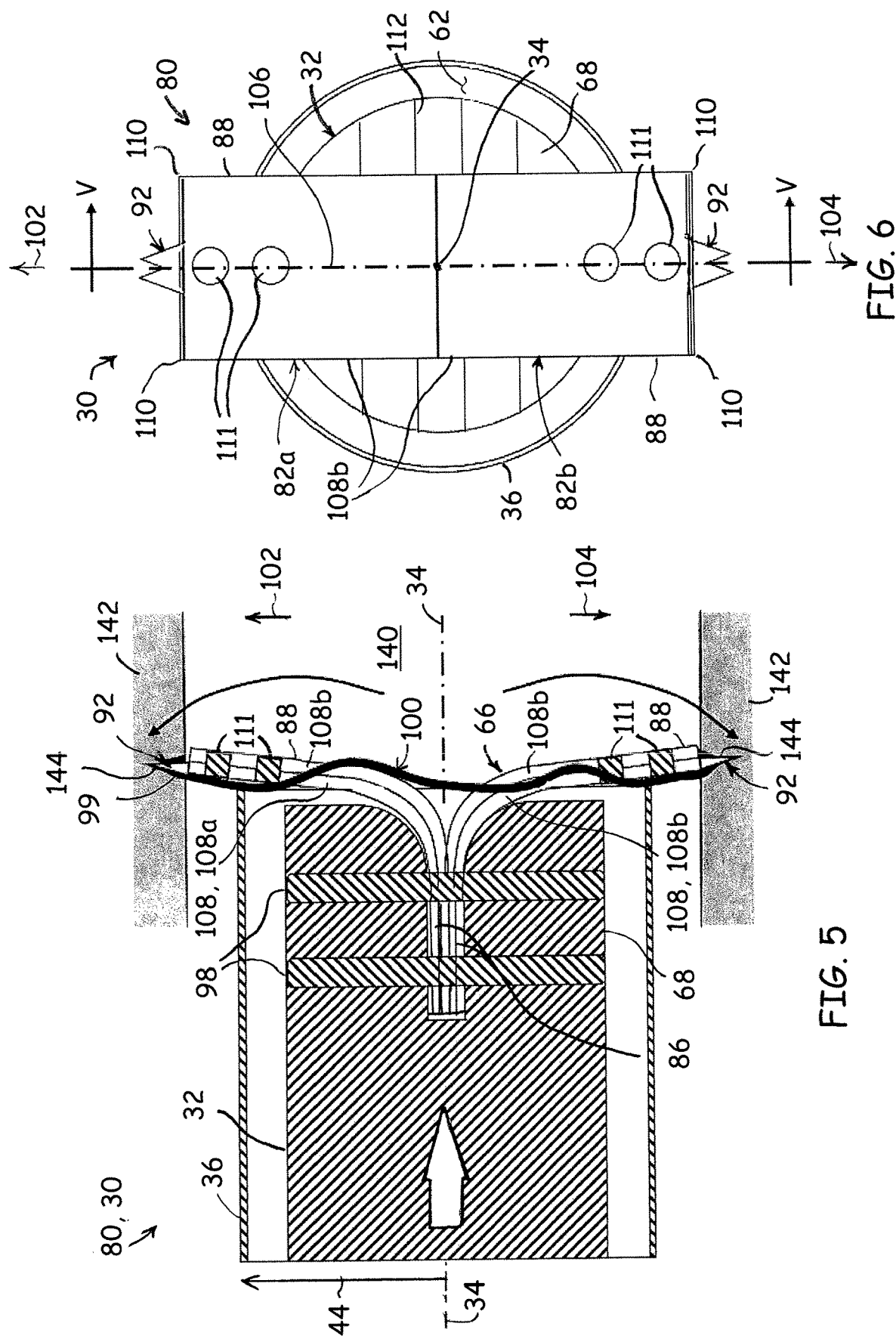

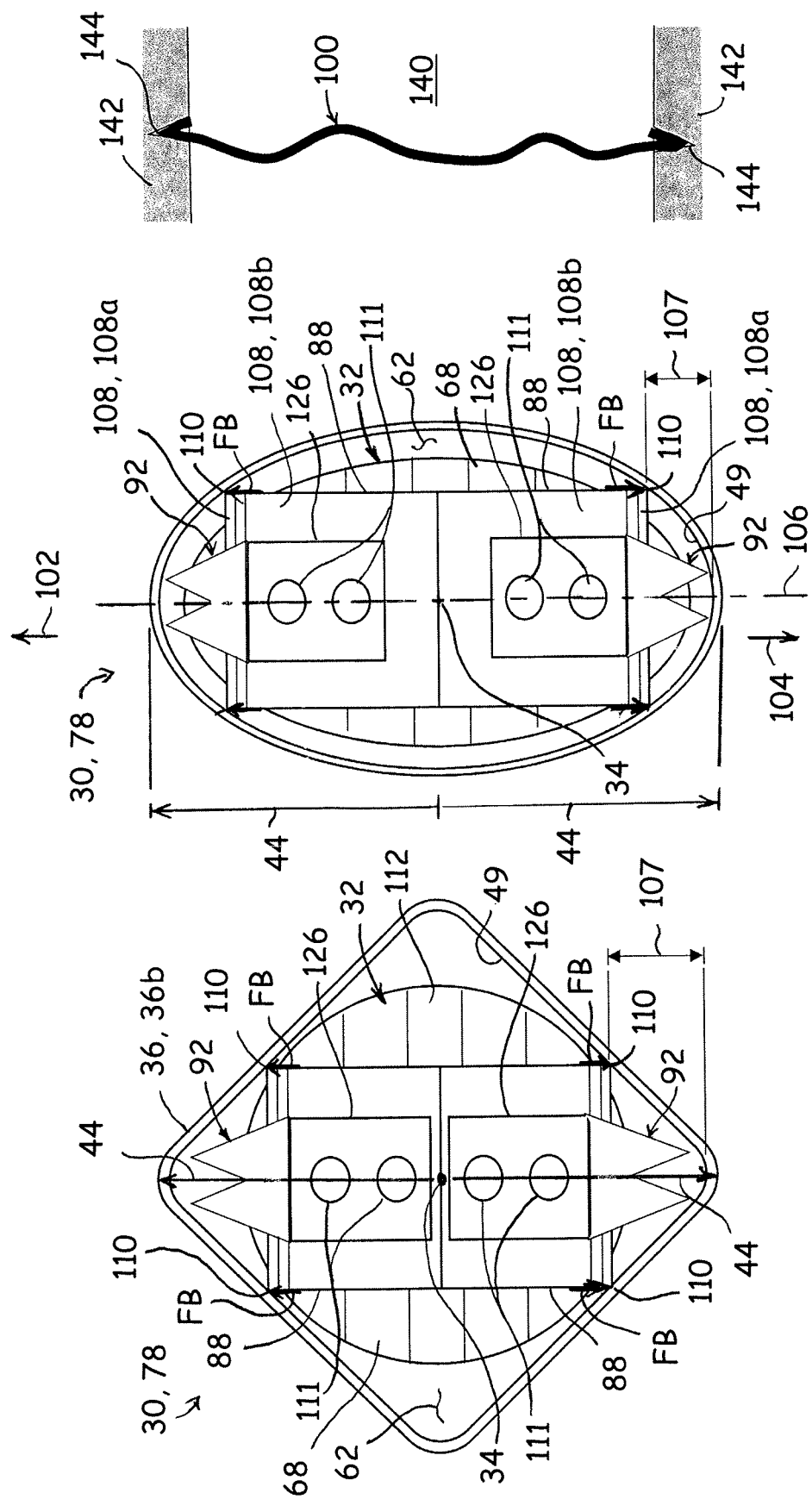

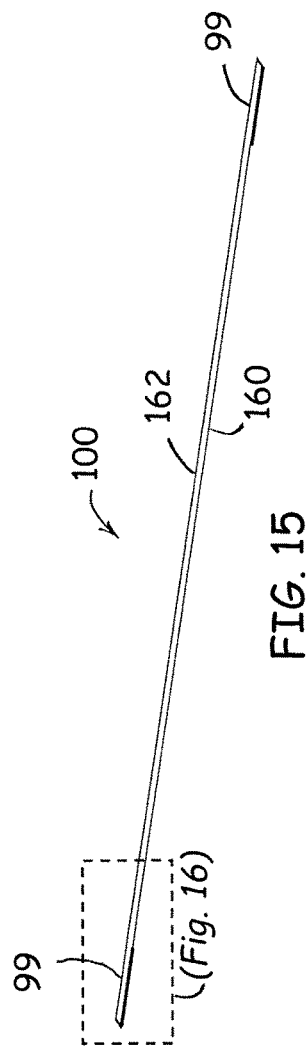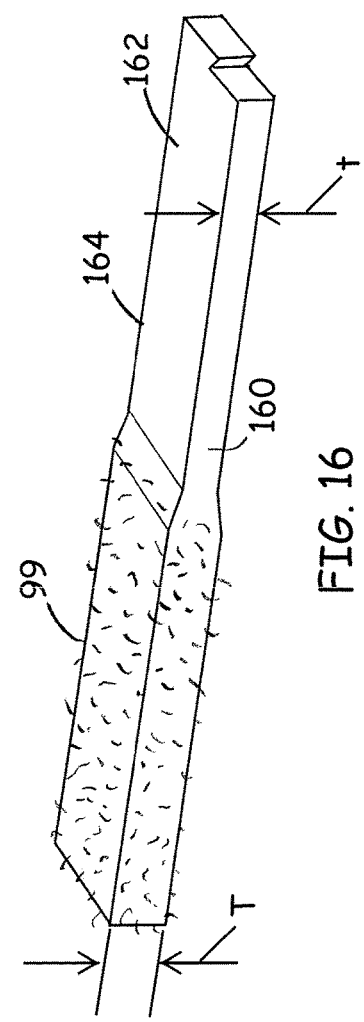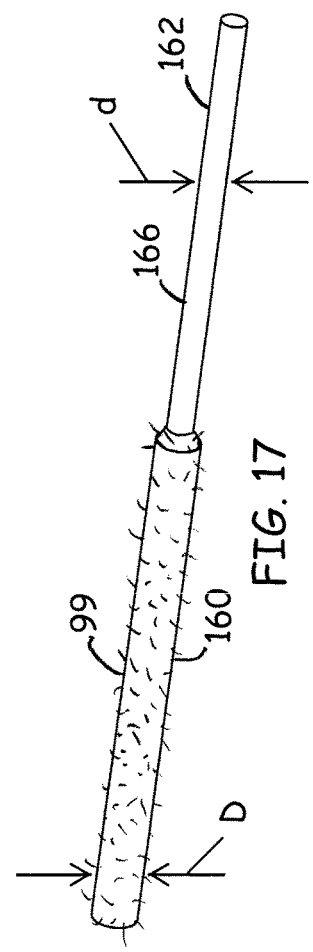

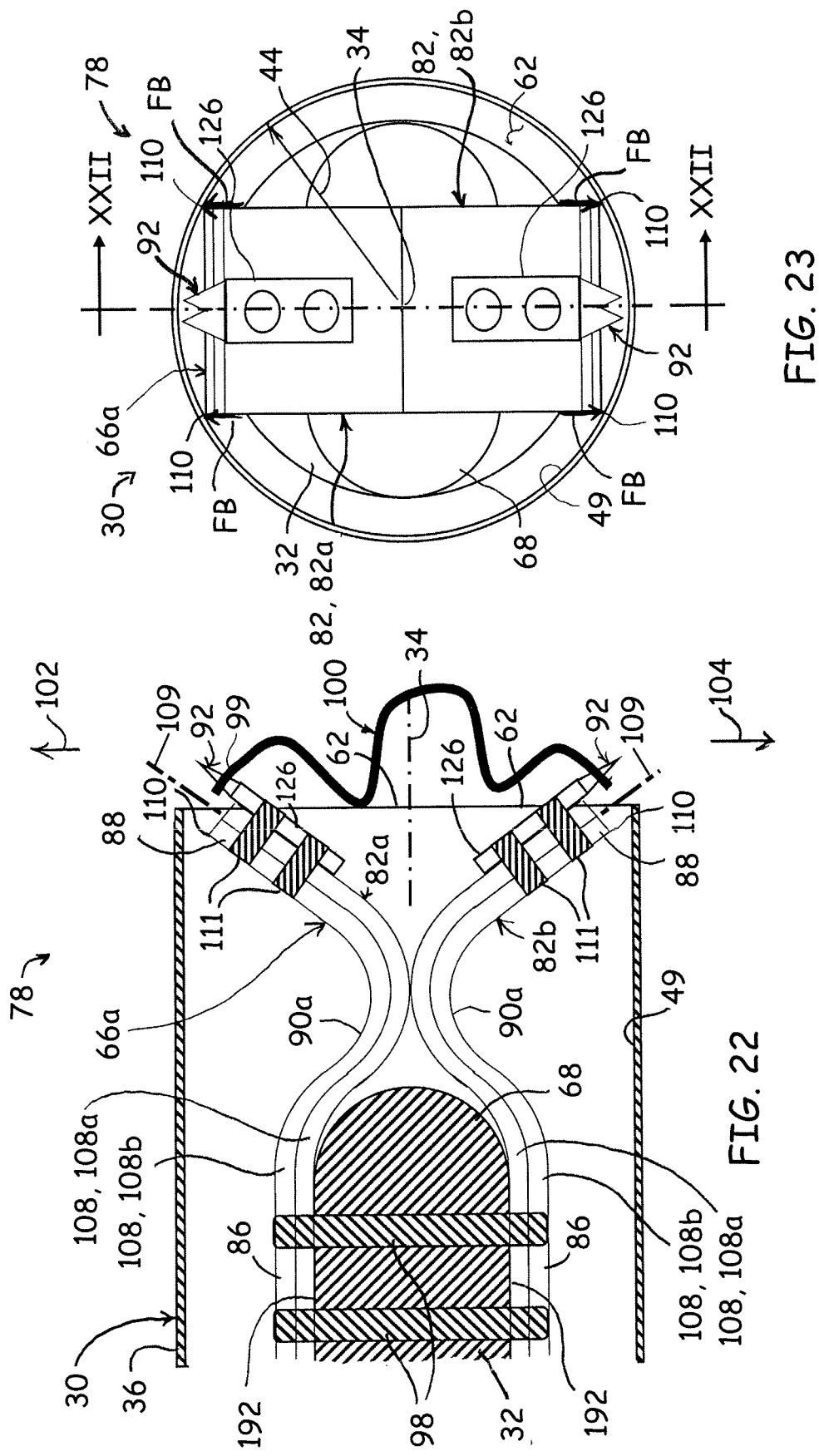

CANNULATED ENDPLATE PLUNGER

RELATED APPLICATIONS

This application claims the benefit of U.S. Provisional Patent Application No. 62/829,690, filed Apr. 5, 2019, and of U.S. Provisional Patent Application No. 62/902,506, filed Sep. 19, 2019, the disclosures of which are incorporated by reference herein in their entirety.

FIELD OF THE DISCLOSURE

The disclosure is directed to methods and tools for spinal fusion therapy, and more specifically to methods and tools for implanting tissue growth-promoting devices between adjacent vertebrae.

BACKGROUND

Spinal fusion (arthrodesis) involves immobilizing the joint between two adjacent vertebrae. Minimally invasive surgical techniques, such as Oblique Lateral Lumbar Interbody Fusion (OLLIF), have been developed, wherein the spinal fusion surgery is performed through a cannulated access, requiring an incision of a mere 15 millimeters in length. Blood loss is reduced by as much as 90% with the OLLIF procedure compared to traditional surgical retraction techniques. A key aspect of minimally invasive techniques is to complete the surgery in a short amount of time, in some cases as little as 30 minutes.

During recovery, new bone tissue grows between the adjacent vertebrae to complete the fusion process. The faster the growth of the new bone tissue, the shorter the recovery period. As such, surgical techniques that promote the growth of the new bone tissue and associated devices and instrumentation that facilitate rapid delivery via a cannulated access would be welcomed.

SUMMARY OF THE DISCLOSURE

Various embodiments of the disclosure include an endplate plunger assembly for implanting a growth-promoting tether between adjacent and opposed vertebral endplates during spinal fusion surgery. Once the disc nucleus is sufficiently cleared from between the opposed adjacent vertebral endplates, the sequence for implanting the growth-promoting tether may be performed quickly, literally in a matter of seconds.

The endplate plunger, which is suitable for cannulated access in minimally invasive surgeries, includes a pair of resilient arm assemblies that, when in a retracted configuration, are elastically deformed to store potential energy therein. In transitioning from the retracted configuration to a deployed configuration, the potential energy stored in the resilient arm assemblies is released suddenly, providing a burst of kinetic energy, which thrusts tip portions of the resilient arm assemblies into the opposed vertebral endplates. The swiftness of the kinetic energy burst is effectively automatic; there is no need for the surgeon to perform a rapid action to create the rapid deployment. Instead, the surgeon need only provide a deliberate action that initiates the conversion of the potential energy into kinetic energy. The deliberate action may be analogized as akin to releasing the string of an archer's bow.

In some embodiments, impingement of the tip portions causes a cleft to be formed on each of the opposed vertebral endplates. The growth-promoting tether may be coupled to the tip portions in a manner that enables opposed ends of the tether to be directly lodged in the clefts, without need for barbs or other anchors to be permanently affixed to the anchor. Upon retraction of the tip portions from the vertebral endplate, the tether is left in place, extending between the opposed vertebral endplates to provide a path along which tissue growth is promoted and accelerated during the natural fusion process.

In some embodiments, the growth-promoting tether is configured to have roughened end portions that enhances the friction between the clefts and the tether. The enhanced friction facilitates release of the tip portions from the tether as the resilient arm assemblies are withdrawn and retracted from the vertebral endplates.

Various embodiments of the disclosure include devices and methods for routing the tether through a spinal implant after the spinal implant is placed. The spinal implant is configured for releasable attachment to a cannula through which an endplate plunger is inserted. The endplate plunger is inserted through the cannula with the tether coupled thereto and positioned within the spinal implant. The spinal implant defines openings that are sized so that the resilient arm assemblies can pass therethrough upon deployment, so that deployment of the endplate plunger causes the tether to be anchored to the adjacent vertebral endplates, thereby extending through the spinal implant.

Structurally, various embodiments of the disclosure include an endplate plunger for anchoring a tether to opposed adjacent end plates of a spine, comprising a sleeve defining an outer radial dimension at an open distal end, a shaft disposed within the sleeve, the shaft being translatable within the sleeve and including a distal end portion that is proximate the open distal end of the sleeve, a first resilient arm assembly affixed to the distal end portion of the shaft, the first resilient arm assembly including a proximal end portion and a distal end portion separated by an arcuate mid portion, the distal end portion of the first resilient arm assembly defining a first notch that is open to a distal extremity of the distal end portion of the first resilient arm assembly, the first notch being configured for releasably mounting a tether thereto, and a second resilient arm assembly affixed to the distal end portion of the shaft, the second resilient arm assembly including a proximal end portion and a distal end portion separated by an arcuate mid portion, the distal end portion of the second resilient arm assembly defining a second notch that is open to a distal extremity of the distal end portion of the second resilient arm assembly, the second notch being configured for releasably mounting the tether thereto. In a deployed configuration, the distal extremity of the first resilient arm assembly extends radially beyond the outer radial dimension of the sleeve in a first radial direction, and the distal extremity of the second resilient arm assembly extends radially beyond the outer radial dimension of the sleeve in a second radial direction, the second radial direction being opposite the first radial direction. In a retracted configuration, the first resilient arm assembly and the second resilient arm assembly are elastically deformed to retract within the outer radial dimension of the sleeve. In some embodiments, the sleeve defines an oblong cross-section.

In some embodiments, the first resilient arm assembly includes a first flexure, and the distal extremity of the first resilient arm assembly includes a first tip portion that defines the first notch and extends from the first flexure. Likewise, the second resilient arm assembly may include a second flexure, and the distal extremity of the second resilient arm assembly includes a second tip portion that defines the second notch and extends from the second flexure. The first tip portion may be a separate component attached to the first flexure and the second tip portion is a separate component attached to the second flexure. Also, the first tip portion may taper to distal points on opposing sides of the first notch, and the second tip portion may taper to distal points on opposing sides of the second notch.

In some embodiments, the first flexure defines and extends along a first termination axis at the distal end portion of the first resilient arm assembly, and the first tip portion extends at a first canted angle relative to the first termination axis. Likewise, the second flexure may define and extend along a second termination axis at the distal end portion of the second resilient arm assembly, and the second tip portion may extend at a second canted angle relative to the second termination axis. The first canted angle may approximate an attack angle of the first tip portion, and the second canted angle may also approximate an attack angle of the second tip portion. In some embodiments, the distal end portion of the first resilient arm assembly and the distal end portion of the second resilient arm assembly each include a contact point that contacts an interior surface of the sleeve when in the retracted configuration.

In various embodiments of the disclosure, a method for anchoring a tether to opposed adjacent vertebrae is presented, comprising: providing an endplate plunger; providing instructions on a tangible, non-transitory medium, the instructions including: forming a first cleft in a first vertebral endplate with the endplate plunger; inserting a first end of a tether into the first cleft with the endplate plunger; forming a second cleft in a second vertebral endplate with the endplate plunger; and inserting a second end of the tether into the second cleft with the endplate plunger, wherein the first end of the tether and the second end of the tether is unitary with a mid-portion of the tether. In some embodiments, the step of forming the first cleft and the step of inserting the first end of the tether into the first cleft are performed simultaneously. The step of forming the first cleft and the step of forming the second cleft may be performed simultaneously.

Various embodiments of the disclosure disclose a growth-promoting tether to promote tissue growth between opposed vertebral endplates, comprising opposing end portions separated by a mid-portion, the opposing end portions being unitary with the mid-portion, the opposing end portions including coarse biocompatible materials. In some embodiments, the coarse biocompatible material are in the form of one of wire fragments and particulates. The opposing end portions may be of a greater dimension than the mid-portion, the greater dimension being one of a thickness and a diameter. As such, growth-promoting tether may be a flat ribbon, and the greater dimension is the thickness. In some embodiments, the growth-promoting tether is a cord having a substantially circular cross-section, and the greater dimension is the diameter. In some embodiments, one of a growth factor and cells are infused into a base material of the growth-promoting tether to promote bone growth. The base material may be one of a woven fabric tubing, a woven mesh, a non-woven mesh, a braided structure, and a woven structure. The coarse biocompatible material may include a biocompatible metal. The coarse biocompatible material may include hard tissue fragments.

In various embodiments of the disclosure, a spinal implant system is disclosed, comprising a spinal implant defining a central axis, the body portion defining a receptacle and including a proximal end portion that defines an access port for accessing the receptacle, the spinal implant including a body portion that defines a superior-inferior plane that is coplanar with the central axis, the body portion defining a superior opening and an inferior opening, each extending into the receptacle and having a lateral width orthogonal to the superior-inferior plane, the lateral width being centered about the superior-inferior plane. The spinal implant system includes a cannula configured for selective attachment to the access port of the spinal implant, the cannula defining a maximum inner dimension. The spinal implant system also includes an endplate plunger having a distal end configured for translation through the cannula and into the receptacle, the endplate plunger including a pair of arm assemblies. In a retracted configuration, the pair of arm assemblies are at or within the maximum inner dimension of the cannula. In a deployed configuration, the pair of arm assemblies extend radially from the central axis beyond the maximum inner dimension and into the superior opening and the inferior opening. In some embodiments, the endplate plunger includes a sleeve having an open distal end. In some embodiments, at least a portion of the pair of arm assemblies extends axially from the opening when in the retracted configuration. The access port of the spinal implant and a distal end of the cannula may be threaded for the selective attachment.

In some embodiments, the endplate plunger includes a sleeve defining an outer radial dimension at an open distal end, and a shaft disposed within the sleeve, the shaft being translatable within the sleeve, wherein the pair of arm assemblies includes a first resilient arm assembly and a second resilient arm assembly, each affixed to a distal end portion of the shaft. Each of the first resilient arm assembly and the second resilient arm assembly may include a proximal end portion and a distal end portion separated by an arcuate mid-portion. In some embodiments, the distal end portion of the first resilient arm assembly and the distal end portion of the second resilient arm assembly each include a contact point that contacts an interior surface of the sleeve when in the retracted configuration. The distal end portion of the first resilient arm assembly may define a first notch that is open to a distal extremity thereof, the distal end portion of the second resilient arm assembly defines a second notch that is open to a distal extremity thereof, and the first notch and the second notch are configured for releasably mounting a respective end of a tether thereto.

In some embodiments, the first resilient arm assembly includes a first flexure, and the distal extremity of the first resilient arm assembly includes a first tip portion that defines the first notch and extends from the first flexure. Likewise, the second resilient arm assembly may include a second flexure, and the distal extremity of the second resilient arm assembly may include a second tip portion that defines the second notch and extends from the second flexure. In some embodiments, the first tip portion is a separate component attached to the first flexure and the second tip portion is a separate component attached to the second flexure. The first tip portion may taper to distal points on opposing sides of the first notch, and the second tip portion may taper to distal points on opposing sides of the second notch.

In some embodiments, the first flexure defines and extends along a first termination axis at the distal end portion of the first resilient arm assembly, and the first tip portion extends at a first canted angle relative to the first termination axis. Likewise, the second flexure may define and extend along a second termination axis at the distal end portion of the second resilient arm assembly. The second tip portion extends at a second canted angle relative to the second termination axis. In some embodiments, the first canted angle approximates an attack angle of the first tip portion and the second canted angle approximates an attack angle of the second tip portion.

In various embodiments of the disclosure, a method for implanting a growth-promoting tether within a spinal implant is disclosed, comprising: providing a kit including a spinal implant, a cannula, and an endplate plunger, and providing instructions on a tangible, non-transitory medium, the instructions including: coupling the cannula to a proximal end of the spinal implant; inserting the spinal implant between adjacent vertebral endplates of a patient; releasably coupling a tether to a pair of extendible arms of the endplate plunger; inserting the endplate plunger axially through the cannula so that a distal end of the endplate plunger is disposed within a receptacle of the spinal implant; deploying the pair of extendible arms within the receptacle to pass through openings of the spinal implant and drive anchor the tether to each of the vertebral endplates. In some embodiments, the instructions include the step of rotationally aligning an actuation plane of the endplate plunger with a plane of the spinal implant, the openings being centered about the plane. The openings of the spinal implant in the step of deploying the pair of extendible arms may be a superior opening and an inferior opening. In some embodiments, the kit includes one or more tethers, which may include growth-promoting material.

BRIEF DESCRIPTION OF THE DRAWINGS

FIG. 3 is an enlarged, partial sectional view of the distal end of an endplate plunger in a retracted configuration at plane III-III of FIG. 4 according to an embodiment of the disclosure;

FIG. 4 is an enlarged end view of the distal end of the endplate plunger in the retracted configuration of FIG. 3 according to an embodiment of the disclosure;

FIG. 5 is an enlarged, partial sectional view of the distal end of the endplate plunger of FIGS. 3 and 4 at plane V-V of FIG. 6 in a deployed configuration according to an embodiment of the disclosure;

FIG. 6 is an enlarged end view of the distal end of the endplate plunger in the deployed configuration of FIG. 5 according to an embodiment of the disclosure;

FIG. 8 is a side view of the distal end portion of the resilient arm assembly of FIG. 7 with a tip portion formed on an outer flexure according to an embodiment of the disclosure;

FIG. 12 is an enlarged end view of a distal end of a retracted endplate plunger having a rounded rectangular tubular sleeve according to an embodiment of the disclosure;

FIG. 13 is an enlarged end view of a distal end of a retracted endplate plunger having an oblong tubular sleeve according to an embodiment of the disclosure;

FIG. 14 is an elevational view of a tether implanted in and connecting vertebral endplates according to an embodiment of the disclosure;

FIG. 15 is a perspective view of a tether for use with the disclosed endplate plungers according to an embodiment of the disclosure;

FIG. 16 is an enlarged, partial perspective view of a distal end portion of the tether of FIG. 15 according to an embodiment of the disclosure;

FIG. 17 is an enlarged, partial perspective view of an alternative distal end portion for a tether according to an embodiment of the disclosure;

FIG. 22 is an enlarged, partial sectional view of a distal end of an endplate plunger at plane XXII-XXII of FIG. 23 in a retracted configuration according to an embodiment of the disclosure;

FIG. 23 is an enlarged end view of the distal end of the endplate plunger in the retracted configuration of FIG. 22 according to an embodiment of the disclosure;

DETAILED DESCRIPTION

Figure 1:
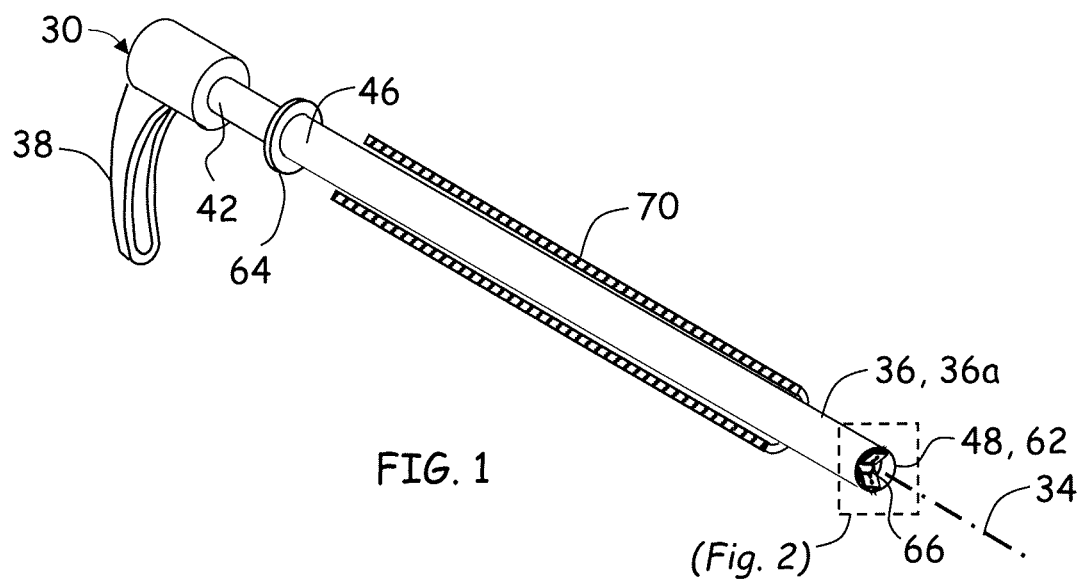
FIG. 1 is a perspective view of a cannulated endplate plunger according to an embodiment of the disclosure.
Figure 2:
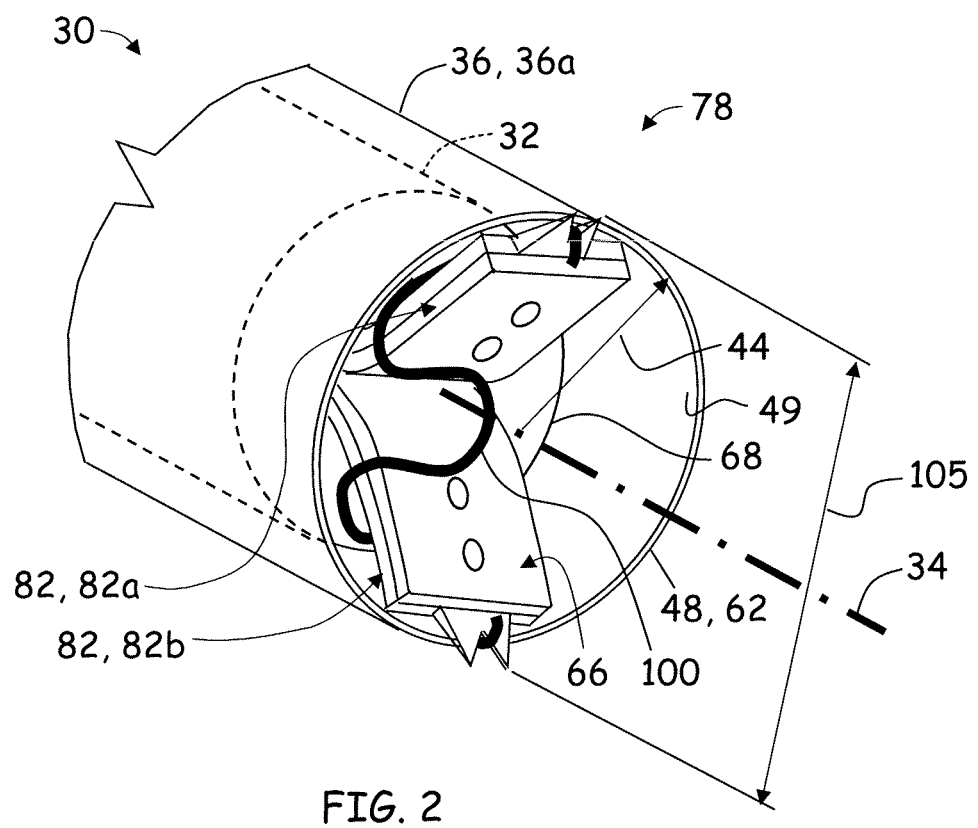
FIG. 2 is an enlarged, partial perspective view of a distal end of the endplate plunger of FIG. 1 according to an embodiment of the disclosure.

Referring to FIGS. 1 and 2, an endplate plunger 30 is depicted according to an embodiment of the disclosure. The endplate plunger 30 includes a shaft 32 that is translatable along a central axis 34, the central axis 34 being defined by a sleeve 36. In some embodiments, a handle 38 is coupled to a proximal end 42 of the shaft 32. The sleeve 36 defines a maximum outer radial dimension 44 about the central axis 34 and includes a proximal end 46, a distal end 48, and an interior surface 49. In some embodiments, the sleeve 36 is of a round tubular stock 36a to define a circular cross-section. As discussed attendant to FIGS. 12 and 13, other cross-sections for the sleeve are contemplated, such as oblong, elliptical, and polygonal.

The distal end 48 defines an opening 62. In some embodiments, a flange 64 is coupled to the proximal end 46. A plunger assembly 66 is coupled to a distal end portion 68 of the shaft 32. In some embodiments, the endplate plunger 30 may also be configured for insertion into a cannula 70.

Referring to FIGS. 3 through 6, the plunger assembly 66 is depicted according to an embodiment of the disclosure. In FIGS. 2, 3, and 4, the endplate plunger 30 is depicted in a retracted configuration 78. In FIGS. 5 and 6, the endplate plunger 30 is depicted in a fully deployed configuration 80. The plunger assembly 66 includes a first resilient arm assembly 82a and a second resilient arm assembly 82b affixed to the distal end portion 68 of the shaft 32. The resilient arm assemblies 82a, 82b are herein referred to collectively or generically as resilient arm assembly or assemblies 82. Each of the resilient arm assemblies 82 includes a proximal end portion 86 and a distal end portion 88 separated by an arcuate mid-portion 90. The distal end portions 88 may each include a tip portion 92 defining a notch 94 that is open to a distal extremity 96 of the tip portion 92 of the respective resilient arm assembly 82. The resilient arm assemblies 82 is affixed to the distal end portion 68 of the shaft 32, for example with rivets or pins 98. The notches 94 may be configured to receive opposed end portions 99 of a tether 100. The tether 100 is removed from FIGS. 4 and 6 for clarity.

In the fully deployed configuration 80, the distal extremity 96 of the first resilient arm assembly 82a extends radially beyond the maximum outer radial dimension 44 of the sleeve 36 in a first radial direction 102, and the distal extremity 96 of the second resilient arm assembly 82b extends radially beyond the maximum outer radial dimension 44 of the sleeve 36 in a second radial direction 104. The first and second radial directions 102 and 104 are opposed. An actuation plane 106 is defined that is coplanar with the central axis 34 and parallel to the first and second radial directions 102 and 104. In the retracted configuration 78, the resilient arm assemblies 82 are elastically deformed to retract to within the maximum outer radial dimension 44 of the sleeve 36. Also in the retracted configuration 78, the plunger assembly defines a retracted radial dimension 105 that extends orthogonal to the central axis 34 (FIG. 2).

In some embodiments, the plunger assembly 66 may be positioned entirely within the sleeve 36 in the retracted configuration 78 (FIG. 3), so that the resilient arm assemblies 82 do not project through the opening 62 when fully retracted. In such embodiments, the tip portions 92 extend into a clearance 107 defined between the resilient arm assemblies 82 and the interior surface 49 of the sleeve 36 (FIG. 4). Alternatively, the plunger assembly 66 partially projects out of the opening 62. For example, at least some of the tip portions 92, may project out of the opening 62 when fully retracted, as depicted at FIG. 22. In some embodiments, the retracted radial dimension 105 of the plunger assembly 66 does not exceed the outer diameter of the sleeve 36 (i.e., does not exceed twice the maximum outer radial dimension 44).

In some embodiments, each resilient arm assembly 82 includes one or more flexures 108 and the tip portion 92. The flexure(s) 108 may define the proximal end portion 86, the distal end portion 88, and the arcuate mid-portion 90. The flexure(s) 108 define and are centered about a termination axis 109 (FIGS. 8 through 11). Embodiments that implement a plurality of flexures 108 include an inner flexure 108a and an outer flexure 108b and may include additional flexures (not depicted) interstitial between the inner and outer flexures 108a and 108b. The inner flexure 108a is the flexure 108 that is closest to the central axis 34; the outer flexure 108b is the flexure 108 that is furthest from the central axis 34. In some embodiments, the flexure(s) 108 define contact points 110, such as exposed corners of the flexure(s) 108 (depicted) proximate the tip portion 92, that contact the interior surface 49 of the sleeve 36 when in the retracted configuration 78. The distal end portion 68 of the shaft 32 may define a slot 112 that is open to a distal extremity 113 of the distal end portion 68 of the shaft 32. In some embodiments, the proximal end portions 86 of the resilient arm assemblies 82 are is disposed within the slot 112. In some embodiments that implement more than one flexure 108 for each resilient arm assembly 82, the plurality of flexures 108 are affixed to each other, for example by the pins 98 at the proximal end portion 86 and with rivets 111 at the distal end portion 88.

Functionally, the elastic deformation in the retracted configuration 78 causes potential energy to be stored in the resilient arm assemblies 82, thereby exerting opposed radially outward biasing forces FB against the interior surface 49 of the sleeve 36. In some embodiments, the biasing forces FB are exerted at the contact between the contact points 110 and the interior surface 49 of the sleeve 36 to register the contact points 110 against the interior surface 49 of the sleeve 36 when in the retracted configuration 78. For embodiments that utilize multiple flexures 108, the flexures 108 may move relative to each other at the arcuate mid-portions 90 during flexing of the resilient arm assemblies 82.

Figure 7:
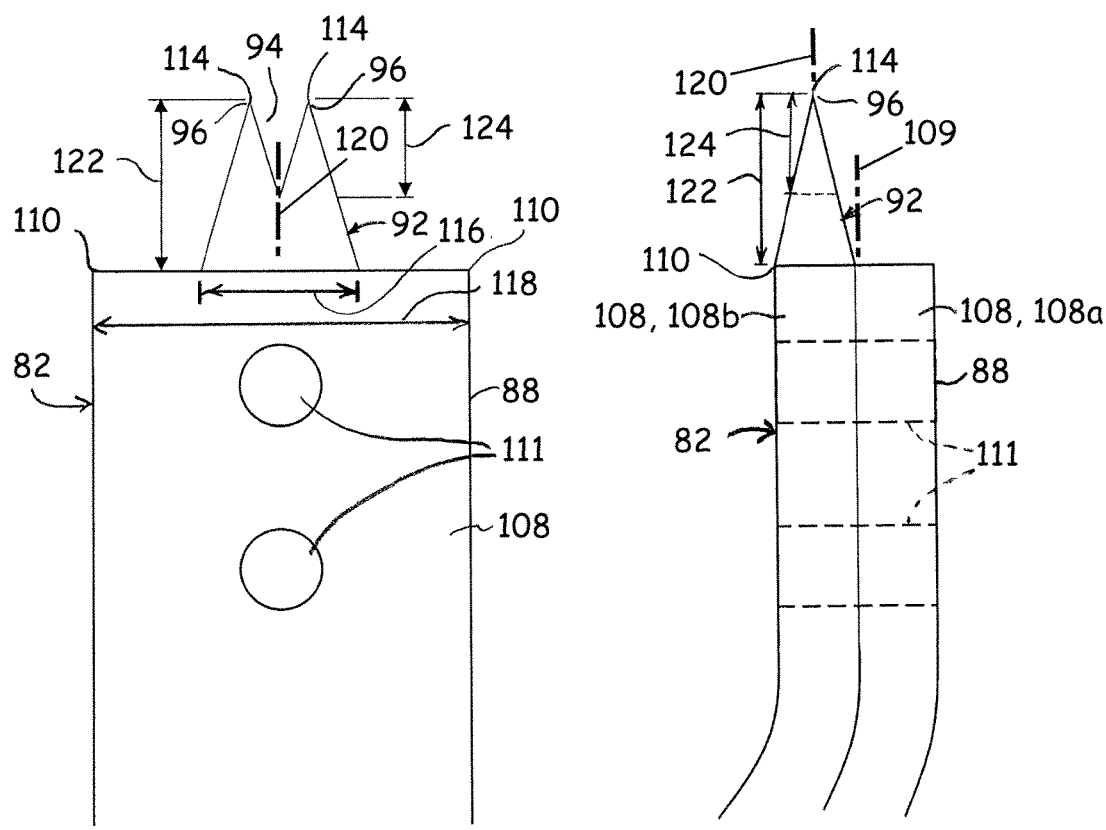
FIG. 7 is an enlarged, plan view representing a distal end portion of a resilient arm assembly according to several embodiments of the disclosure.

Referring to FIG. 7, a representation of the distal end portion 88 of various resilient arm assemblies 82 is depicted according to an embodiment of the disclosure. In some embodiments, the tip portion 92 tapers to distal points or edges 114 on opposing sides of the notch 94. The tip portion 92 may be of a reduced lateral dimension 116 relative to a full lateral width 118 of the flexures 108 that separates the contact points 110. The tip portion 92 defines and extends along a tip axis 120, and may extend beyond the contact points 110 to define a length 122 parallel to the tip axis 120. In some embodiments, the length 122 of the tip portion 92 is in a range of 2 millimeters to 8 millimeters inclusive. In some embodiments, the length 122 of the tip portion 92 is in a range of 3 millimeters to 7 millimeters inclusive. In some embodiments, the length 122 of the tip portion 92 is in a range of 4 millimeters to 6 millimeters inclusive. The notch 94 defines a depth 124 along the tip portion 92 relative to the distal points or edges 114 and parallel to the tip axis 120. The depth 124 of the notch 94 is configured and dimensioned to grip a respective one of the opposed end portions 99 of the tether 100 when mounted in the notch 94.

Referring to FIGS. 8 through 11, alternative configurations for the distal end portion 88 of the resilient arm assemblies 82 are depicted according to embodiments of the disclosure. In embodiments utilizing a plurality of flexures 108, the tip portion 92 may be formed on and unitary with the outer flexure 108b (FIG. 8), the inner flexure 108a (FIG. 9), or on an intermediate flexure (not depicted). In embodiments including the plurality of flexures 108 and having the tip portion 92 formed on one of the flexures 108, the flexure 108 upon which the tip portion is formed (e.g., outer flexure 108b in FIG. 8) extends beyond the other of the plurality of flexures 108 (e.g., beyond flexure 108a in FIG. 8) so that the tip portion 92 protrudes at the distal extremity 96 of the resilient arm assembly 82. For the embodiments of FIGS. 8 through 11, the tip axis 120 and termination axis 109 are substantially parallel.

Figures 9, 10:
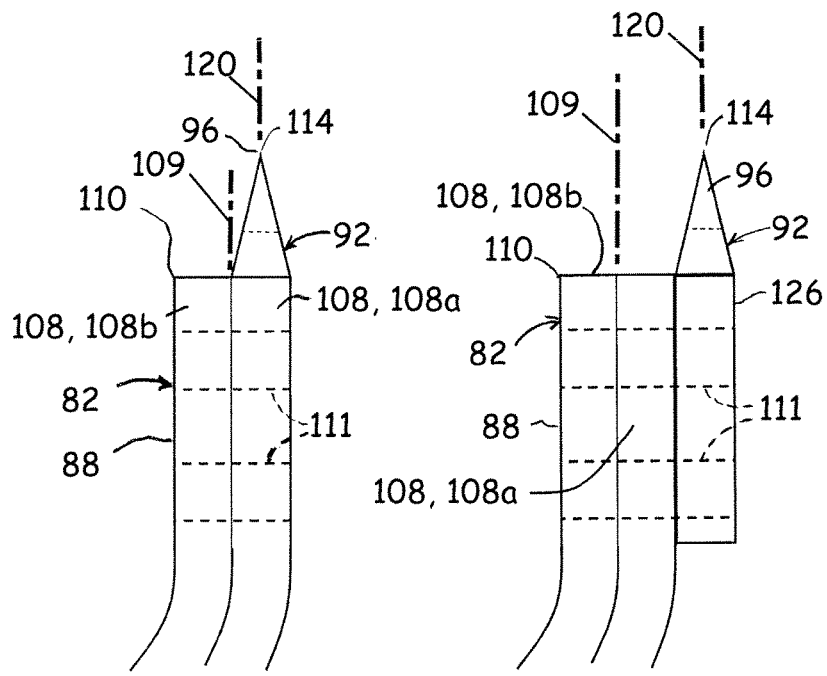
FIG. 9 is a side view of the distal end portion of the resilient arm assembly of FIG. 7 with a tip portion formed on an inner flexure according to an embodiment of the disclosure.
FIG. 10 is a side view of the resilient arm assembly of FIG. 7 with a separate tip portion affixed to an inner flexure according to an embodiment of the disclosure.
Figure 11:
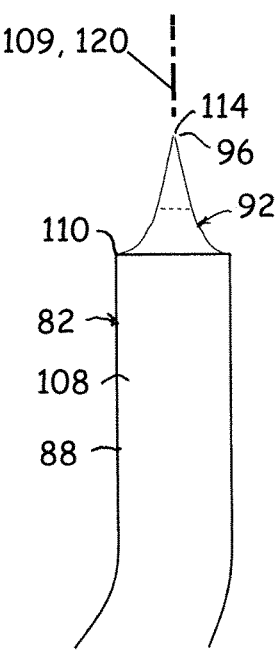
FIG. 11 is a side view of the distal end portion of a single flexure resilient arm assembly with a tip portion formed thereon according to an embodiment of the disclosure.

Each tip portion 92 may be a separate component 126 that is attached to the respective flexure(s) 108 (FIG. 10; also FIGS. 22-25). The notch 94 and points or edges 114 may be defined by the separate component 126 tip portion 92. When formed as a separate component 126, the tip portion 92 may be affixed to the flexures 108 with rivets 128, for example the rivets 111 that affix the plurality of flexures 108 together at the distal end portion 88 of the resilient arm assembly 82. In some embodiments, the separate component 126 tip portion 92 is disposed on the inner flexure 108a of the plurality of flexures 108 (depicted). Optionally, the separate component 126 tip portion 92 is disposed on the outer flexure 108b of the plurality of flexure(s) 108 (not depicted).

In some embodiments, a single flexure 108 may be utilized for each resilient arm assembly 82 (FIG. 11) instead of a plurality of flexures, with the tip portion 92 formed at the distal end portion 88 of the single flexure 108. Alternatively, the separate component 126 tip portion 92 may be joined to the single flexure 108 with rivets (not depicted). In yet another alternative arrangement, the single flexure 108 may be shaped to have the same profile as FIG. 10 with the tip portion 92 being unitary with the single flexure 108.

Referring to FIGS. 12 and 13, end views of the distal end portions 88 of endplate plungers 30 with sleeves 36 having non-circular cross-sections are depicted according to embodiments of the disclosure. The distal end portions 88 of FIGS. 12 and 13 include many of the same components and attributes as the distal end portion 88 of FIG. 4, which are indicated with same-numbered reference characters. Instead of being constructed of round tubular stock 36a as depicted in FIGS. 1 through 6, the sleeve 36 may be of a non-circular stock. By way of non-limiting example, such the non-circular stock includes rounded rectangular tubular stock 36b (FIG. 12) and oblong (e.g., elliptical) tubular stock 36c (FIG. 13).

Functionally, for the same maximum outer radial dimension 44 and the same full lateral width 118 for the flexures 108, the non-circular stock 36b and 36c provide greater clearance 107 for housing the tip portions 92 in the retracted configuration 78. That is, the contact points 110 register against the interior surface 49 at a location that is closer to the central axis 34 of the sleeve 36, thereby increasing the clearance 107. The greater clearance 107 enables the length 122 of the tip portion 92 (FIG. 7) to be increased, enabling the use of longer length 122 for the tip portions 92, which can drive deeper into the vertebral endplates 142. The functionality of registering and sliding the contact points 110 against the interior surface 49 may be maintained, as depicted.

In some embodiments, the resilient arm assemblies 82 are formed from a biocompatible alloy having substantial shape recovery characteristics. The shape recovery alloy may be an alloy of nickel and titanium such as, for example, NITINOL® strip material. NITINOL® material exhibits substantially full shape recovery (i.e., recovered elongation when strained from about 6%-10%, which is a factor of ten better than the recovered elongation at these strain levels of stainless steel). Other suitable shape recovery alloys include TINEL®.

The shape recovery alloy of the resilient arm assemblies 82 are configured to default to the shape of the fully deployed configuration 80. That is, absent any external forces or constraints, the resilient arm assemblies 82 will assume the shape of the fully deployed configuration 80.

Referring to FIG. 14 and again to FIGS. 3 through 6, operation of the endplate plunger 30 is depicted according to an embodiment of the disclosure. With the plunger assembly 66 in the retracted configuration 78, the distal end 48 of the sleeve 36 is inserted into a void 140 between opposed adjacent vertebral endplates 142, the void 140 having been evacuated and prepared by methods available to the artisan. In some embodiments, access for insertion of the distal end 48 is provided by the cannula 70. The endplate plunger 30 is rotationally oriented about the central axis 34 so that the actuation plane 106 is substantially parallel to a sagittal plane of the patient. With the distal end 48 in a desired axuak position and rotational orientation between the vertebral endplates 142, the shaft 32 is translated distally toward the opening 62, so that the contact points 110 of the resilient arm assemblies 82 slide along the interior surface 49 and toward the opening 62.

Upon passing through the opening 62, the sleeve 36 no longer opposes the resilient arm assemblies 82, so that the potential energy stored in the elastically deformed resilient arm assemblies 82 while in the retracted configuration 78 is released. The potential energy is released in the form of kinetic energy, driving the resilient arm assemblies 82 toward the fully deployed configuration 80. The kinetic energy thrusts the tip portions 92 beyond the maximum outer radial dimension 44 of the sleeve 36 and into the vertebral endplates 142 (FIG. 5). The tip portions 92 carry the opposed end portions 99 of the tether 100, lodging the end portions 99 into the vertebral endplates 142.

To remove the endplate plunger 30 from the void 140, the shaft 32 is translated proximally within the sleeve 36. Interaction between the distal end portions 88 of the resilient arm assemblies 82 and the distal end 48 of the sleeve 36 at the opening 62 causes the tip portions 92 to be retracted radially inward, away from the vertebral endplates 142 as the distal end portions 88 are drawn into the opening 62 to assume the retracted configuration 78. The inward radial retraction removes the tip portions 92 from the vertebral endplates 142, leaving behind a cleft 144 formed in each of the vertebral endplates 142. The radial retraction also dislodges the end portions 99 of the tether 100 from the tip portions 92, leaving the end portions 99 disposed in the clefts 144. The tether 100 is thereby moored to both vertebral endplates 142 (FIG. 14).

Functionally, driving the opposed end portions 99 of the tether 100 directly into the vertebral endplates 142 avoids the complication and expense of fitting each tether 100 with anchoring hardware. The direct insertion can also better augment tissue growth between the tether 100 and the vertebral end plates 142 at the penetration site than with systems that incorporate anchoring hardware. For embodiments implementing the reduced lateral dimension 116 for the tip portions 92, less force is required to drive the tip portion 92 into the vertebral endplates than for embodiments that present a tip portion having the full lateral width 118 of the flexures 108. The length 122 of the tip portion 92 establishes a depth of the cleft 144 formed in the vertebral endplates 142.

Referring to FIGS. 15 through 17, the tether 100 is depicted in more detail according to embodiments of the disclosure. The tether 100 is flexible and may be made of an absorbent base material 160, fabricated, for example, as woven fabric tubing, woven or non-woven mesh, braided or woven structures, or some combination thereof. Growth factors or cells can be infused or otherwise incorporated into the base material 160 to promote bone growth along the tether 100. Growth factors can be, for example, transforming growth factor β1, insulin-like growth factor 1, platelet-derived growth factor, fibroblast growth factor, bone morphogenetic protein (BMP), LIM mineralization protein (LMP) and combinations thereof.

The tether 100 includes the opposed end portions 99 separated by a mid-portion 162. The tether 100 may be of any of a variety of forms, including a flat or ribbon form 164 (FIG. 16) and a substantially circular cord form 166 (FIG. 17). The opposed end portions 99 may be impregnated with a coarse biocompatible material, such as biocompatible metals (e.g., titanium, NITINOL®, stainless steel) or hard tissue fragments (e.g., bone). The coarse biocompatible material may be of a variety of forms, including particulate, wire fragments, or a weave. The impregnation of the coarse biocompatible material may cause the opposed end portions 99 to increase in dimension relative to the mid-portion 162 (depicted). For example, a thickness T of the end portions 99 of the ribbon form 164 may be of a greater dimension than a thickness t of the mid-portion 162 (FIG. 16), or a diameter D of the end portions 99 of the substantially circular cord form 166 may be of a greater dimension than the diameter d of the mid-portion 162 (FIG. 17).

Functionally, the impregnation of the coarse biocompatible material effectively roughens and increases the friction of the opposed end portions 99. Increasing the friction facilitates the release of the opposed end portions 99 from the tip portions 92 as the resilient arm assemblies 82 are retracted after implantation of the tether 100 into the vertebral endplates 142. Increasing the friction of the opposed end portions 99 will favor coupling within the soft and plyable clefts 144 over coupling to the smoother and harder tip portions 92, thereby favoring release of the tether 100 from the tip portions 92. In some embodiments, the material impregnated in the end portions 99 help contrast the end portions in fluoroscopic images, which can aid in general visualization of the end portions 99 as well as confirm adequate anchoring within the vertebral endplate 142.

Figure 19:
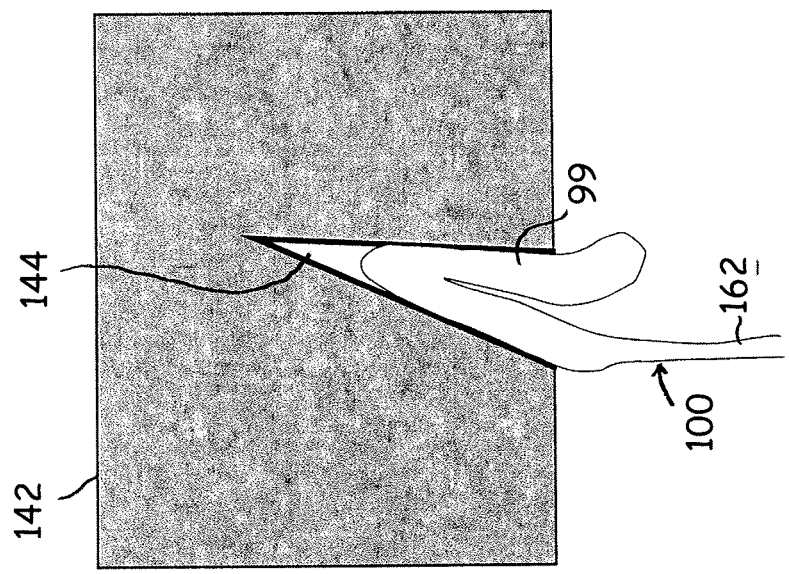
FIG. 19 is an enlarge side view of the tether moored in the vertebral endplate of FIG. 18 after withdrawal of the plunger arm according to an embodiment of the disclosure.
Figure 18:
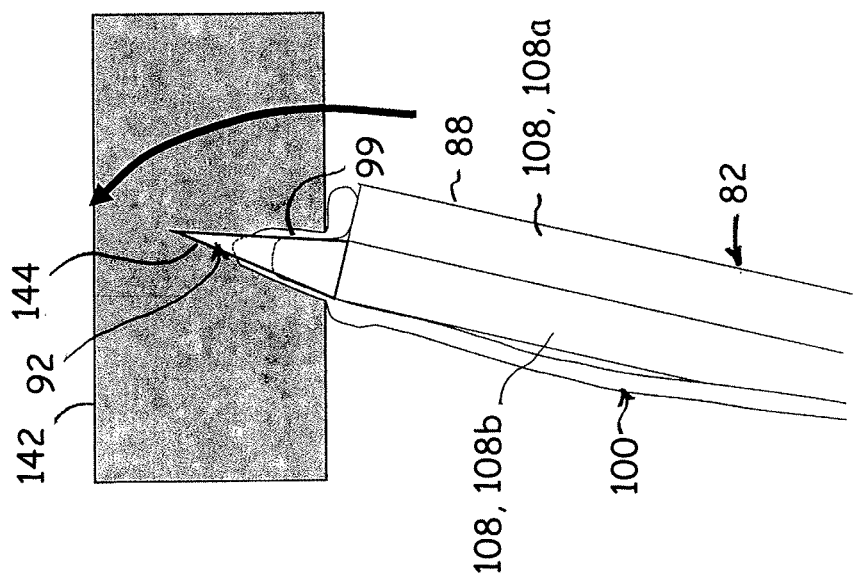
FIG. 18 is an enlarged side view of a plunger arm driving a tether into a vertebral endplate according to an embodiment of the disclosure.

Referring to FIGS. 18 and 19, implantation of the tether 100 into the vertebral endplate 142 is depicted in greater detail according to an embodiment of the disclosure. The burst of kinetic energy caused by release of the resilient arm assembly 82 causes the tip portion 92 to be thrust into the vertebral endplate 142, forming the cleft 144 in the vertebral endplate 142. The notch 94, which carries the end portion 99 of the tether 100, disposes the end portion 99 into the cleft 144. The end portion 99 is compressed between the vertebral endplate 142 and the tip portion 92 of the resilient arm assembly 82 (FIG. 18). Friction holds end portion 99 within the cleft 144 as the tip portion 92 is removed. For embodiments with the coarse biocompatible material, the friction between the end portion 99 and the cleft 144 may be enhanced to a greater extent than the friction between the end portion 99 and the tip portion 92, thereby facilitating the release of the tether 100.

After the tip portion 92 is removed from the cleft 144, the end portion 99 at least partially expands into the cleft 144 (FIG. 19). Also, the cleft 144 partially constricts on the end portion 99 in the absence of the tip portion 92. The combination of the friction of the end portion 99, the expansion of the end portion 99, and the constriction of the cleft 144 acts to secure the tether 100 to the vertebral endplate 142.

Figure 20:
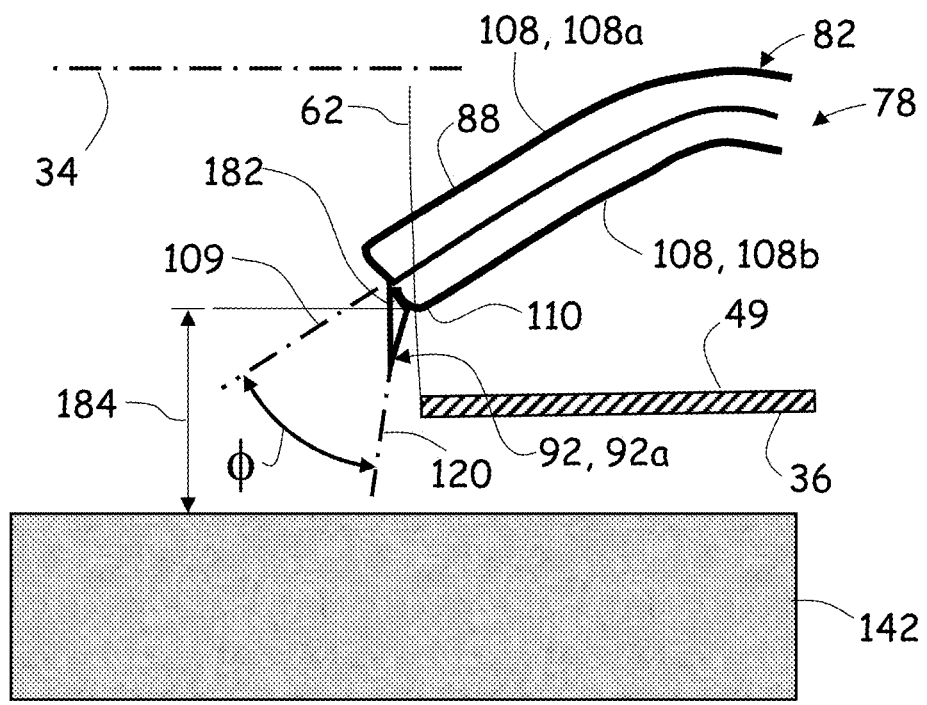
FIG. 20 is an enlarged partial side view of a resilient plunger arm assembly with a canted tip and in a retracted configuration according to an embodiment of the disclosure.
Figure 21:
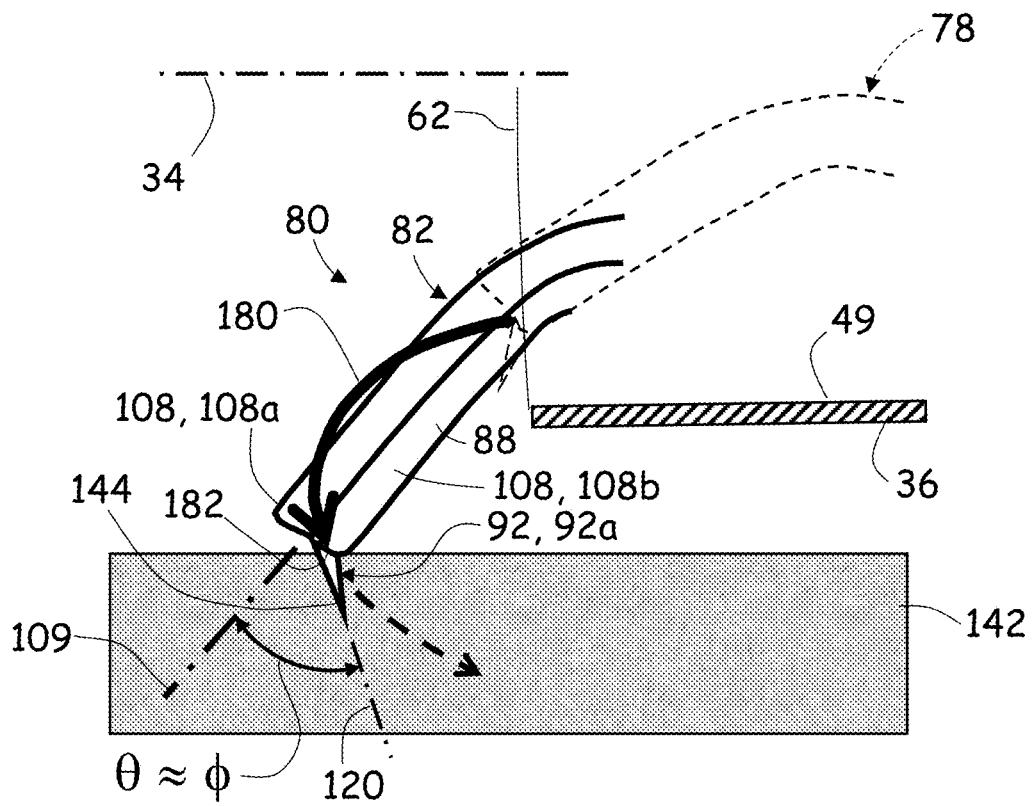
FIG. 21 is an enlarged partial side view of the canted tip of the resilient plunger arm assembly of FIG. 20 being thrust into a vertebral endplate according to an embodiment of the disclosure.
Figure 25:
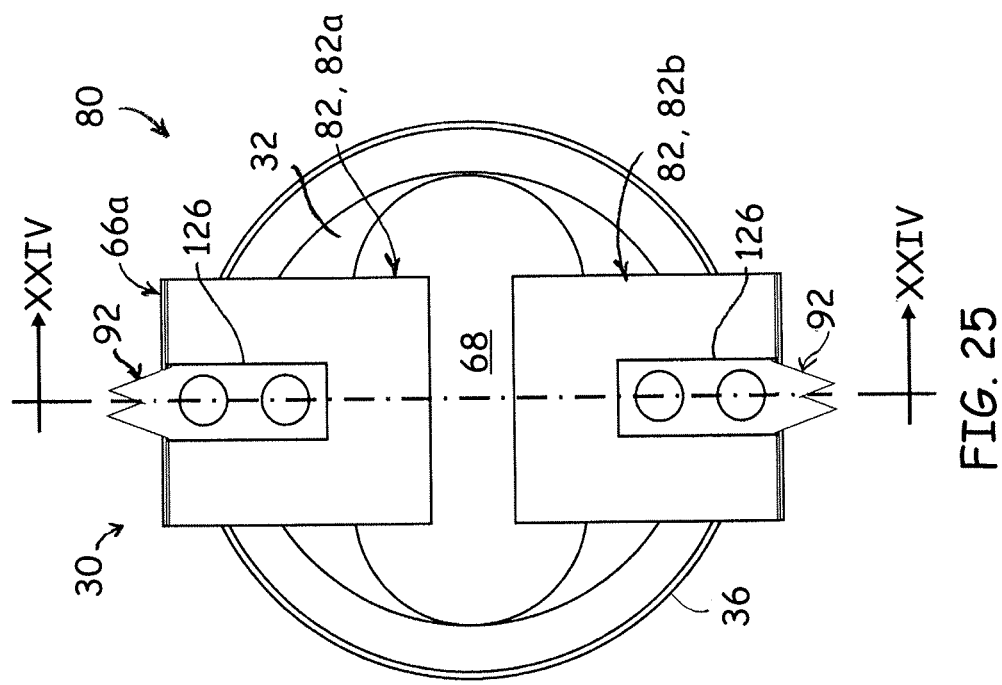
FIG. 25 is an enlarged end view of the distal end of the endplate plunger of FIGS. 22 and 23 in the deployed configuration of FIG. 24 according to an embodiment of the disclosure.
Figure 24:
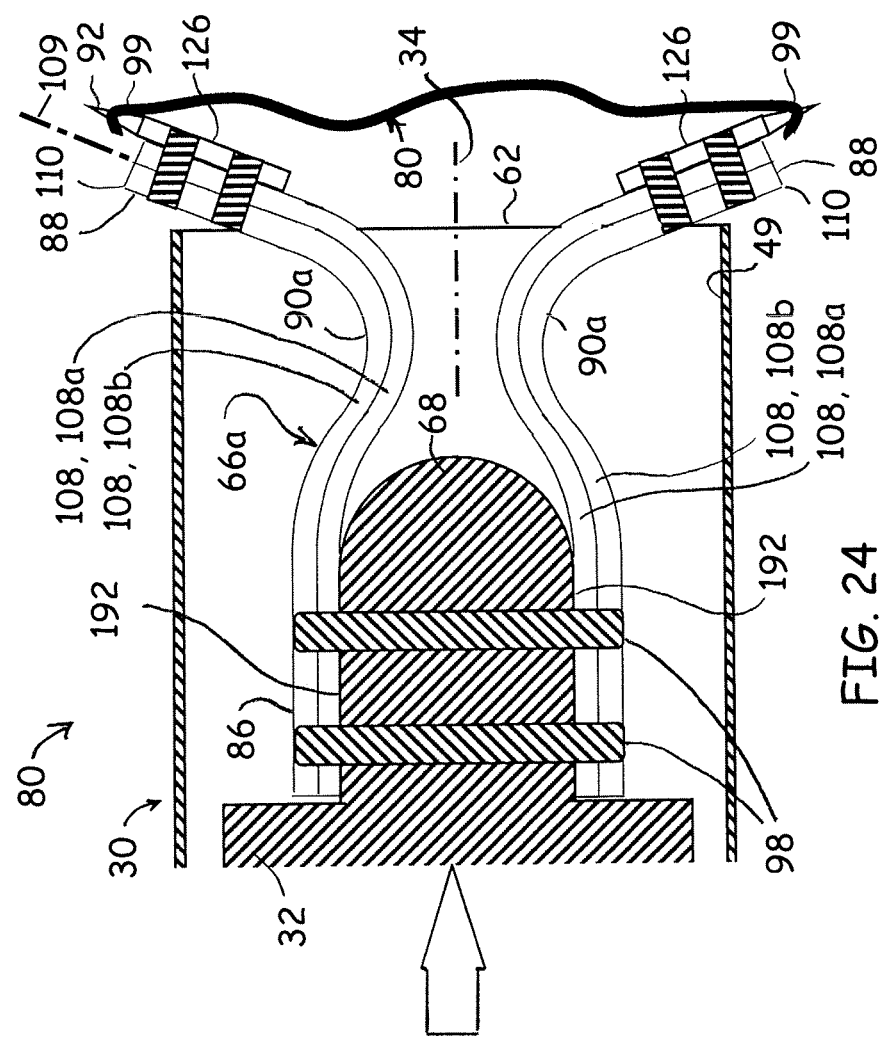
FIG. 24 is an enlarged, partial sectional view of the distal end of an endplate plunger of FIGS. 22 and 23 at plane XXIV-XXIV of FIG. 25 in a deployed configuration according to an embodiment of the disclosure.

Referring to FIGS. 20 and 21, a canted tip portion 92a and the thrusting motion of the resilient arm assemblies 82 are depicted according to an embodiment of the disclosure. The canted tip portion 92a is characterized by a non-zero canted angle φ defined between the tip axis 120 and the termination axis 109. For clarity, FIGS. 20 and 21 depict only the tip portion 92, 92a and the distal end portion 88 of just one of the resilient arm assemblies 82, and a portion of the sleeve 36 and opening 62.

In the retracted configuration 78 (FIG. 20), the contact points 110 of the distal end portion 88 are poised at the opening 62 immediately prior to releasing the potential energy stored in the resilient arm assembly 82. Upon crossing the opening 62, the potential energy is released and the tip portion 92 is thrust into the vertebral endplate 142, following a thrust path 180 (FIG. 21). In FIG. 21, the thrust path 180 traces the path of the distal end portion 88 at a base 182 of the tip portion 92 as the resilient arm assembly 82 springs from the retracted configuration 78 to the deployed configuration 80.

In some embodiments, the thrust path 180 does not follow a constant radius arc. Rather, the thrust path may follow an arc of varying radius (depicted), akin to a partial trace of an ellipse. As such, the tip portion 92 may enter the vertebral endplate 142 at an attack angle θ relative to the termination axis 109 of the flexure(s) 108 at the base of the tip portion 92 that varies substantially, depending on where on the thrust path 180 the vertebral endplate 142 intercepts the distal end portion 88 of the resilient arm assembly 82. In FIGS. 20 and 21, the interception of the distal end portion 88 is characterized by a separation distance 184 between the contact points 110 of the distal end portion 88 and the vertebral endplate 142. The interception of the distal end portion 88 may occur at any point along the thrust path 180, depending on the separation distance 184. The trajectory of the thrust path 180 beyond the illustrated interception is depicted in phantom in FIG. 21.

Accordingly, the canted angle φ may be configured to approximate the attack angle θ, as depicted at FIG. 21. The tip axis 120 need not be in exact alignment with the thrust path 180 at the point of penetration of the vertebral endplate 142. Rather, configuring the canted angle φ to approximate the attack angle θ for a range of typical separation distances 184 may improve performance of the endplate plunger 30.

The canted tip portion 92*a* is depicted in FIGS. 20 and 21 as extending from the outer flexure 108*b* of the plurality of flexure(s) 108, i.e., the tip configuration of FIG. 8. It is understood that the canted tip portion 98 may be utilized with any of the configurations depicted herein, including those of FIGS. 8 through 11.

Referring to FIGS. 22 through 25, an alternative plunger assembly 66*a* is depicted according to an embodiment of the disclosure. The tether 100 is removed from FIGS. 23 and 25 for clarity. The plunger assembly 66*a* includes many of the components and attributes as the plunger assembly 66 of FIGS. 3 through 6, which are indicated with same-numbered reference characters. The plunger assembly 66*a* also operates on the same principles and in the same manner as the plunger assembly 66. One distinction of the plunger assembly 66*a* relative to the plunger assembly 66 is the definition of smaller bend radii across a mid-portion 90*a*. Another distinction is that the proximal end portions 86 of the flexure(s) 108 are mounted to external flats 192 formed on the distal end portion 68 of the shaft 32. The combination of the smaller radii and the external mounting of the flexure(s) 108 also introduce multiple inflection points in the flexure(s) 108, as opposed to a single inflection point for the plunger assembly 66.

Functionally, the change in the geometry of the mid-portion 90*a* may affect the attack angle θ (FIG. 21) at the vertebral endplates 142. The geometry may also influence the forces exerted as the tip portions 92 are thrust into the vertebral endplates 142. The proximal end portions 86 of the resilient arm assemblies 82 are thus affixed to diametrically opposed sides of the shaft 32, providing an option for manufacturing and assembly.

The tip portion 92 of the plunger assembly 66*a* as depicted includes the separate component 126 attached to the respective flexure(s) 108, as depicted in FIG. 10. The plunger assembly 66*a* also illustrates an embodiment where the tip portions 92 extend through the opening 64 when in the retracted configuration 78. However, it is understood that any of the tip configurations depicted herein may be implemented with the plunger assembly 66*a*, and that the plunger assembly 66*a* may be implemented in embodiments where the tip portions 92 are positioned proximate the opening when in the retracted configuration 78. The plunger assembly 66*a* may also be implemented with any of the sleeves 36 depicted or described herein, including those of circular as well as non-circular form.

Figure 26:
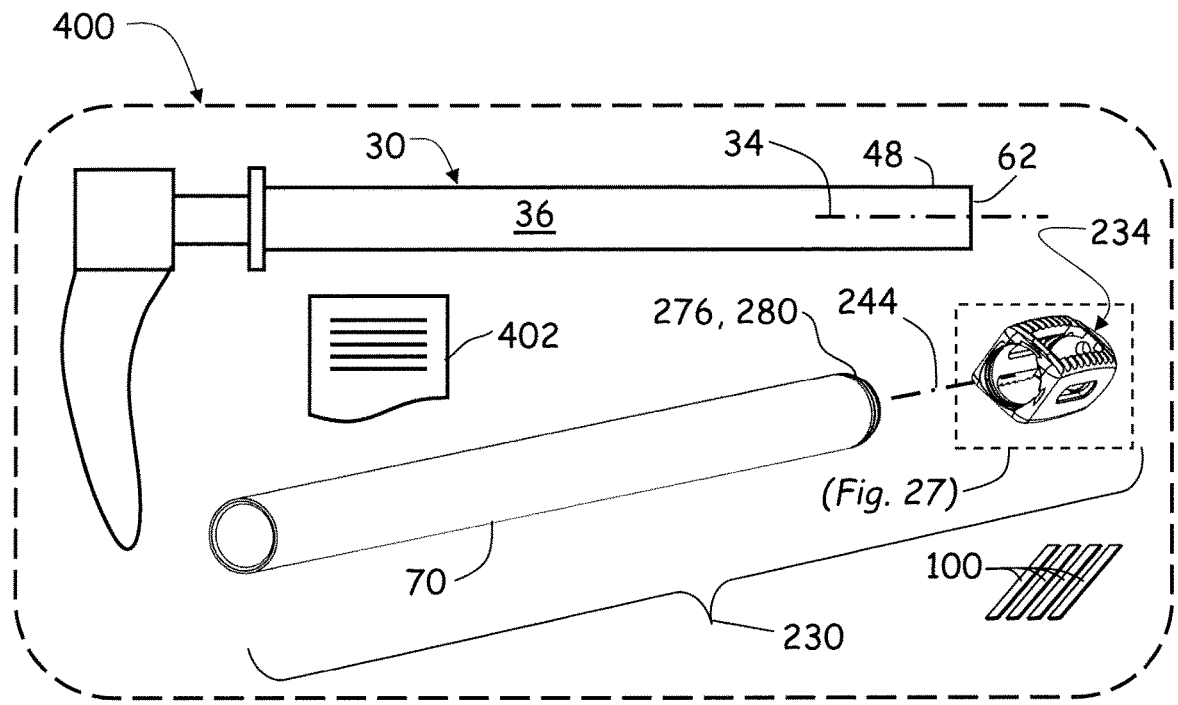
FIG. 26 is a schematic of a kit for deploying a tether within a spinal implant and including a perspective, exploded view of a cannulated spinal implant sub-assembly according to an embodiment of the disclosure.
Figure 27:
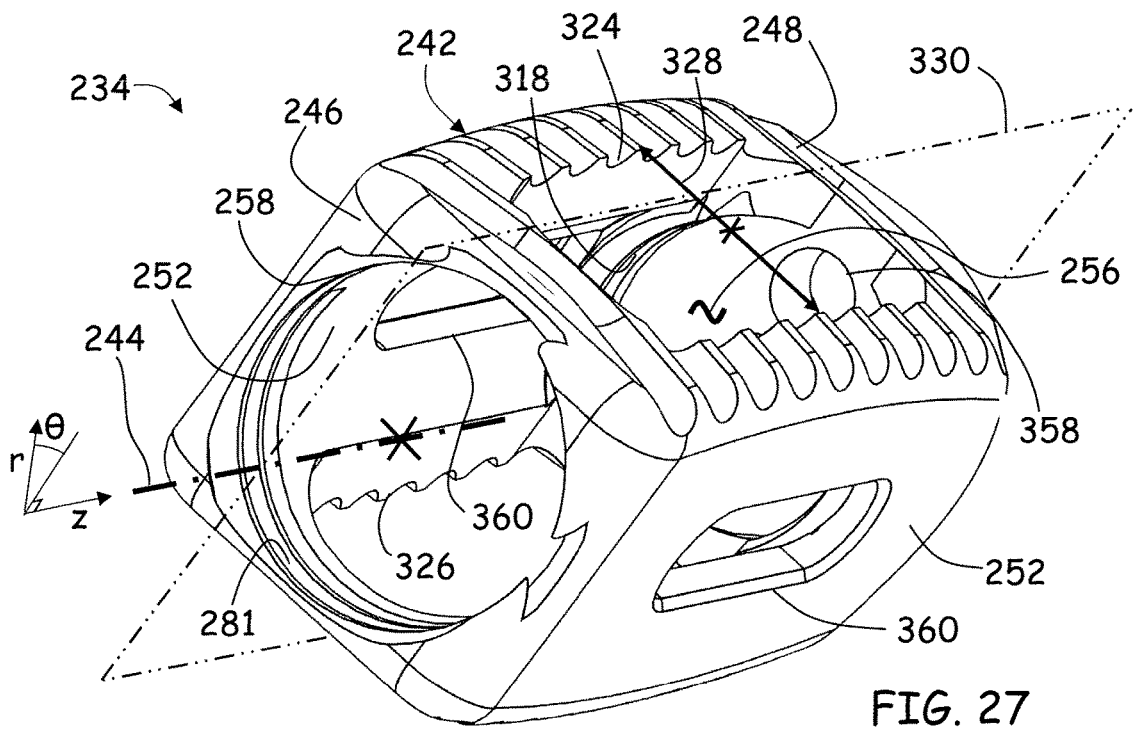
FIG. 27 is an enlarged perspective view of the spinal implant of FIG. 26 according to an embodiment of the disclosure.

Referring to FIGS. 26 and 27, a cannulated spinal implant sub-assembly 230 including the cannula 70 and an accompanying spinal implant 234 for use with the endplate plunger 30 is depicted according to an embodiment of the disclosure. The spinal implant 234 includes a body portion 242 defining a central axis 244 that extends from a proximal end portion 246 through a distal end portion 248 of the body portion 242. The body portion 242 includes side walls 252 that separate the proximal and distal end portions 246, 248. The body portion 242 defines a receptacle 256 accessible via an access port 258 at the proximal end portion 246. The body portion 242 defines a superior opening 324 and an inferior opening 326, each defining a respective lateral dimension 328 that is orthogonal to the central axis 244. The body portion 242 also defines a superior-inferior plane 330 that is coplanar with the central axis 244 and passes through the center of the lateral dimensions 328.

The cannula 70 defines a maximum inner dimension 279. The depicted cannula 70 defines a circular cross-section for accommodating endplate plungers 30 with sleeves 36 of round tubular stock 36*a*, such as depicted in FIG. 1. As such, the maximum inner dimension 279 is the inner diameter of the cannula 70. Cannulas of other shapes are contemplated, for example conforming to the shape of rounded rectangular tubular stock 36*b* of FIG. 12 or the oblong (e.g., elliptical) tubular stock 36*c* of FIG. 13. Cannulas having non-circular shapes define maximum inner dimensions 279 that are not a circular diameter, for example the inner diagonal dimension between opposed corners of a rounded rectangular cannula, or the inner major diameter of an elliptical cannula. The retracted radial dimension 105 of the plunger assembly 66 is less than the maximum inner dimension 279 of the cannula 70.

The cannula 70 may include a distal portion 276 configured for selective attachment to the access port 258 of the spinal implant 234, for example with threads 280 at the distal end 276 that mate with threads 281 formed at the access port 258. The access port 258 is dimensioned to enable passage of the maximum outer radial dimension 44 (FIG. 2) of the sleeve 36 of the endplate plunger 30, thereby enabling passage of the endplate plunger 30 through the cannula 70 when in the retracted configuration 78. The receptacle 256 may be dimensioned to enable translation of the distal end 48 of the sleeve 36 of the endplate plunger 30 within the spinal implant 234 and along the central axis 244 when the endplate plunger 30 is in the retracted configuration 78. In some embodiments, the openings 324 and 326 each define a lateral dimension 328 that enables the full lateral width 118 (FIG. 7) of the flexures 108 to pass therethrough when the endplate plunger 30 transitions from the retracted configuration 78 to the deployed configuration 80. The lateral dimension 328 may be oversized relative to the full lateral width 118 of the flexures 108 to provide margin for a predetermined rotational misalignment between the actuation plane 106 of the endplate plunger 30 (FIGS. 4 and 6) and the superior-inferior plane 330 of the spinal implant 234.

The spinal implant 234 may include additional features, such as a nose portion 304, a through-passage 302, an internal mounting port 318, lock pin recess 358, and side windows 360, identified in FIGS. 26 through 28A. These features and their functions are described further at U.S. Provisional Patent Application No. 62/902,506 to Abbasi, owned by the owner of the present application and incorporated by reference above, and at International Application Publication No. WO 2018/112324 to Abbasi, the disclosure of which is hereby incorporated by reference herein in its entirety except for patent claims and express definitions contained therein.

Referring to FIGS. 28A through 28F, operation of the cannulated spinal implant sub-assembly 230 in conjunction with the endplate plunger 30 is depicted according to an embodiment of the disclosure. While plunger assembly 66 is depicted in FIGS. 28A through 28F, endplate plungers 30 utilizing the plunger assembly 66*a* may also be implemented in the described manner. In some embodiments, the subassembly 230 and endplate plunger 30 may be provided as part of a kit 400 that includes instructions 402.

Figure 28A:
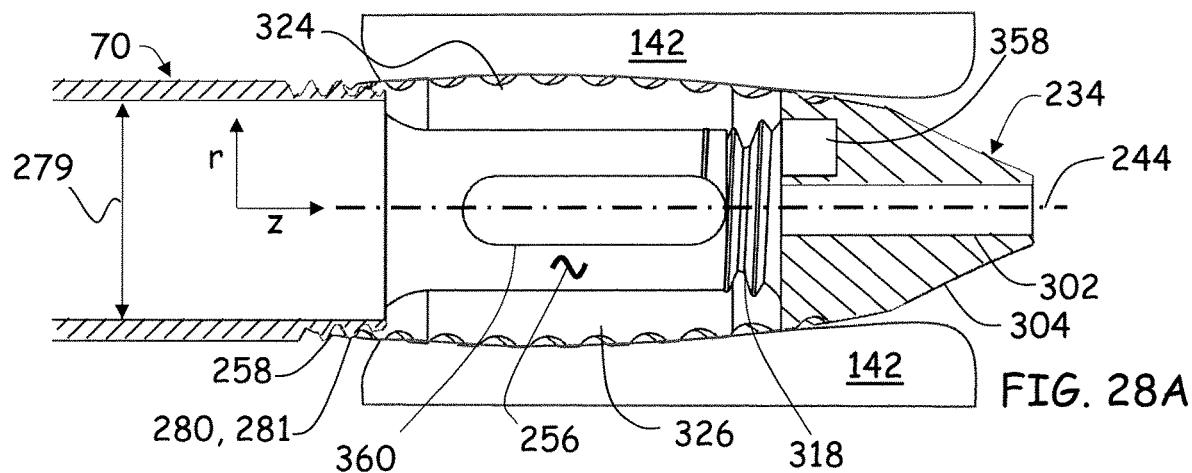
FIG. 28A is an elevational partial sectional view of the cannulated spinal implant sub-assembly of FIG. 26 assembled and inserted between adjacent vertebral endplates according to an embodiment of the disclosure.
Figure 28B:
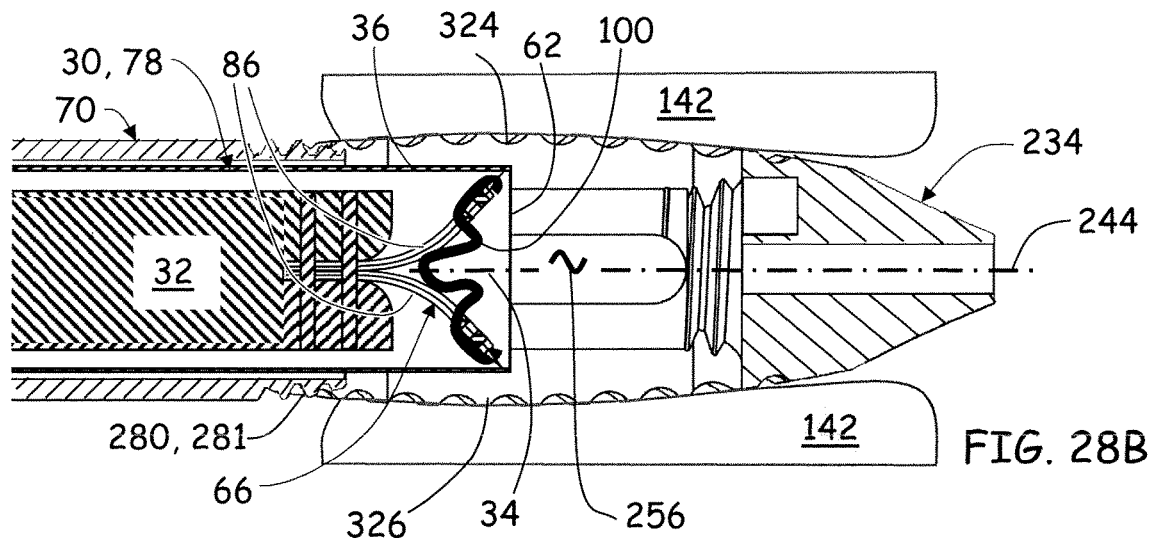
FIG. 28B is an elevational partial sectional view of the inserted cannulated spinal implant sub-assembly of FIG. 28A with the distal end of an endplate plunger of FIG. 3 in a retracted configuration inserted therethrough and positioned for deployment of a growth-promoting tether according to an embodiment of the disclosure.
Figure 28C:
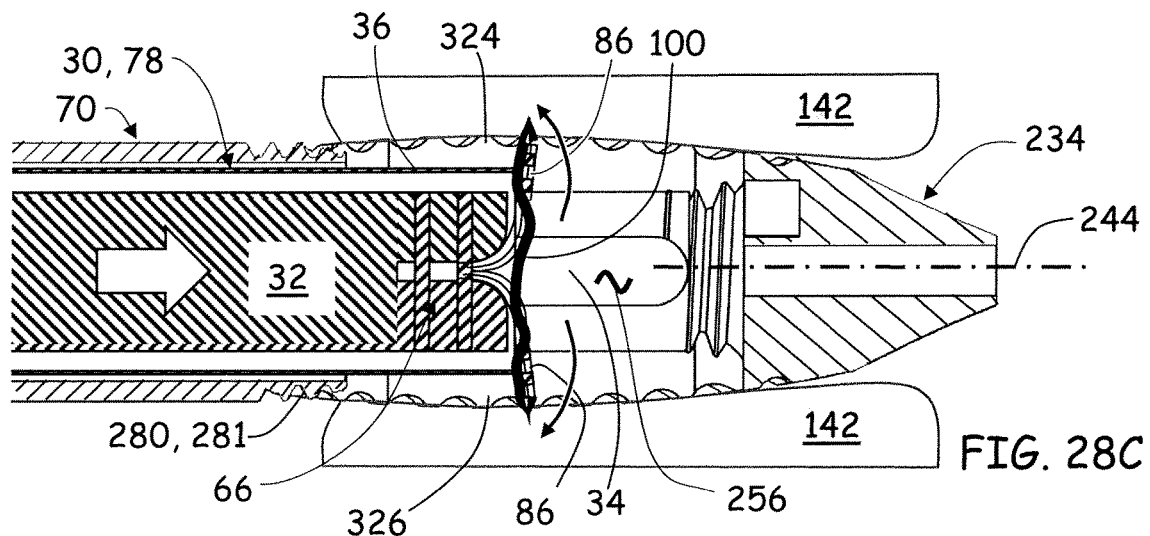
FIG. 28C is an elevational partial sectional view of the inserted cannulated spinal implant sub-assembly of FIG. 28B with the distal end of the endplate plunger in a deployed configuration to implant the growth-promoting tether and connect the vertebral endplates according to an embodiment of the disclosure.

In some embodiments, the spinal implant 234 is implanted between the two adjacent vertebral endplates 142 with the cannula 70 selectively attached, for example with threads 280 (FIG. 28A). The spinal implant 234 may be arranged so that the openings 324 and 326 are each adjacent a respective one of the endplates 142, thereby defining superior and inferior openings 324 and 326, respectively. The growth-promoting tether 100 is releasably coupled to the tip portions 92 of the resilient arm assemblies 82 of the endplate plunger 30. The endplate plunger 30 is inserted into the cannula 70 and translated along the central axis 244 until the distal end 48 of the sleeve 36 extends into the receptacle 256 of the spinal implant 234 so that the opening 62 of the sleeve 36 is positioned between the superior and inferior openings 324 and 326 (FIG. 28B). The endplate plunger 30 may be rotated so that actuation plane 106 of the plunger assembly 66 (FIG. 4) is substantially aligned with the superior-inferior plane of the spinal implant 234 (FIG. 27), preventing the spinal implant 234 from interfering with passage of the resilient arm assemblies 82 through the superior and inferior openings 324 and 326 upon deployment of the plunger assembly 66. In some embodiments, the sleeve 36 and cannula 70 are configured for passive rotational alignment, for example by polygonal cross sections (e.g., the rounded rectangular sleeve 36b of FIG. 12 within a rounded rectangular cannula).

Figure 28D:
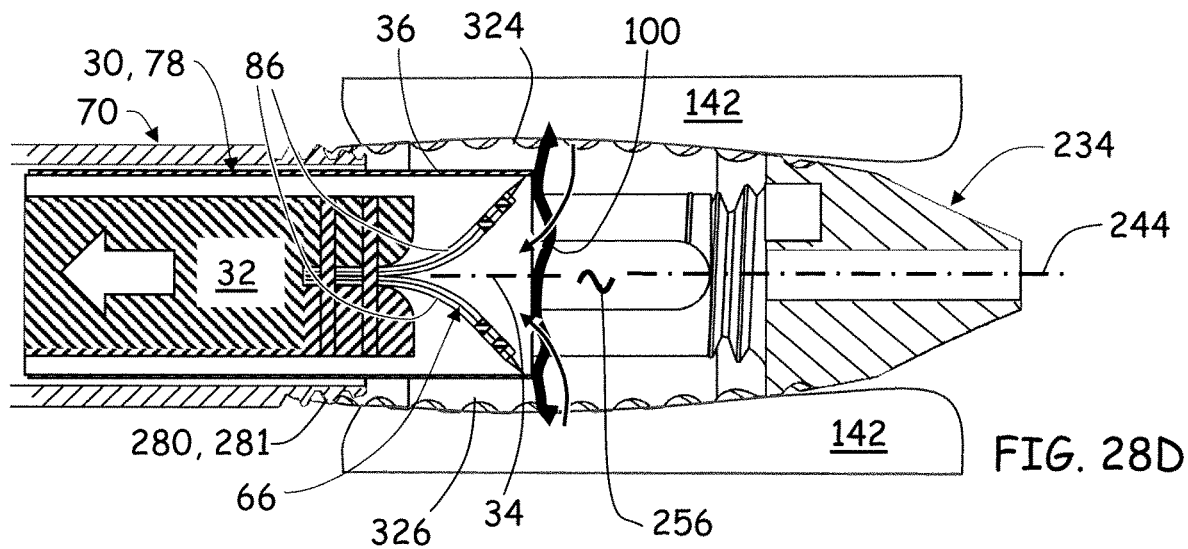
FIG. 28D is an elevational partial sectional view of the inserted cannulated spinal implant sub-assembly of FIG. 28C with the distal end of the endplate plunger retracted after implantation of the growth-promoting tether according to an embodiment of the disclosure.
Figure 28E:
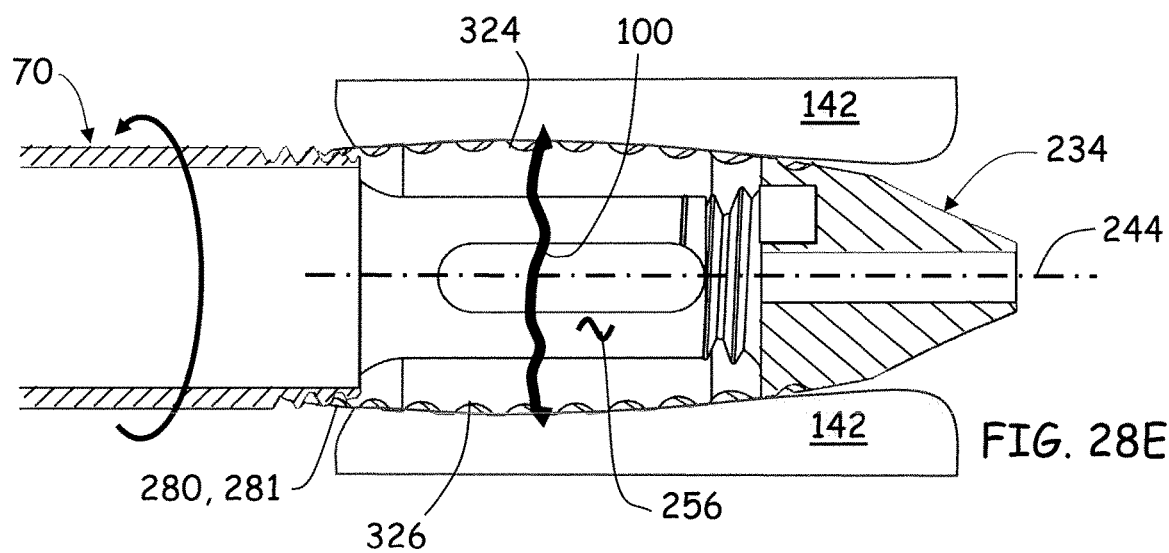
FIG. 28E is an elevational partial sectional view of the inserted cannulated spinal implant sub-assembly of FIG. 28D with the endplate plunger removed after implantation of the growth-promoting tether and depicting the decoupling of the cannula from the spinal implant according to an embodiment of the disclosure.
Figure 28F:
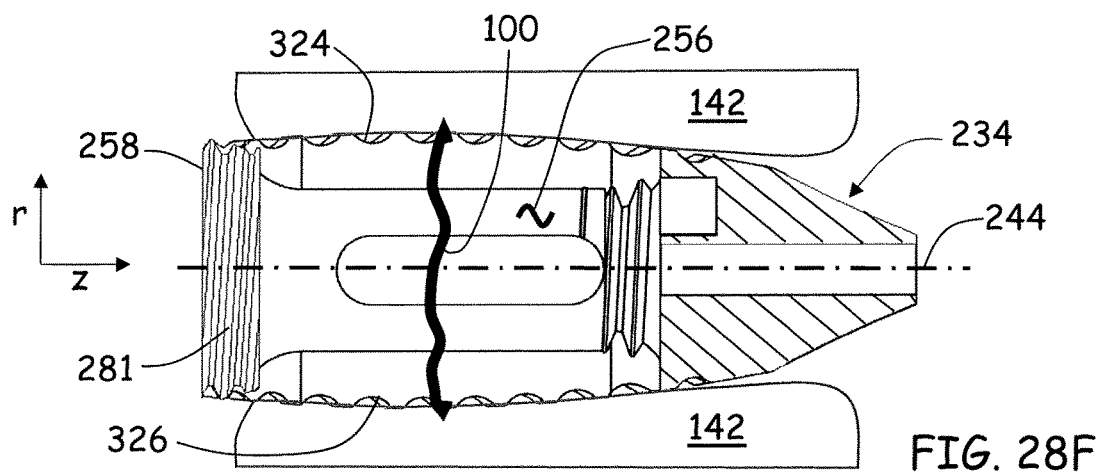
FIG. 28F is an elevational sectional view of the spinal implant and growth-promoting tether of FIG. 28E with the cannula removed after implantation of the growth-promoting tether according to an embodiment of the disclosure.

With the distal end 48 of the sleeve 36 axially and rotationally aligned, and stationary, the plunger assembly 66 is deployed. The resilient arm assemblies 82 exit the opening 62, causing the potential energy stored in the resilient arm assemblies 82 to be released. The release causes the resilient arm assemblies 82 to be thrust through the openings 324 and 326 to impinge the vertebral endplates 142 (FIG. 28C), implanting the tether 100 in the adjacent vertebral endplates 142. The resilient arm assemblies 82 are then retracted, decoupling the tether 100 from the resilient arm assemblies 82 (FIG. 28D). The mechanics of anchoring and release are described attendant to FIGS. 18 and 19. With the plunger assembly 66 in the retracted configuration 78, the endplate plunger is withdrawn from the cannula 70. The cannula 70 is decoupled from the spinal implant 234, for example by unscrewing the threads 280, 281 (FIG. 28E). The cannula 70 is withdrawn, leaving the spinal implant 234 in place with the growth-promoting tether 100 extending therethrough and providing a growth path between the adjacent vertebral endplates 142.

Implantation of the tether 100 as depicted in FIGS. 28A through 28F is not limited to the endplate plunger 30. Other tools that lend themselves to the cannulated delivery into the spinal implant 234 and deployment of tethers or other growth paths through the openings 324 and 326 may be implemented, for example the endplate plunger depicted and described at U.S. patent application Ser. No. 16/239,035 to Abbasi et al., which is owned by the owner of the current application and is hereby incorporated by reference herein in its entirety except for patent claims and express definitions contained therein.

In some embodiments, operation of the endplate plunger 30 as described herein and the subsequent implantation of the tether 100 as described herein are provided as instructions provided on a tangible, non-transitory medium, for example the instructions 402 of kit 400. Non-limiting examples of a tangible, non-transitory medium include a paper document or computer-readable media including compact disc and magnetic storage devices (e.g., hard disk, flash drive, cartridge, floppy drive). The computer-readable media may be local or accessible over the internet. The instructions 402 may be complete on a single medium or divided among two or more media. For example, some of the instructions 402 may be written on a paper document that instruct the operator to access one or more of the operational steps over the internet, the internet-accessible steps being stored on a computer-readable medium or media. The instructions may be in the form of written words, figures, and/or video presentations.

Each of the additional figures and methods disclosed herein can be used separately, or in conjunction with other features and methods, to provide improved devices and methods for making and using the same. Therefore, combinations of features and methods disclosed herein may not be necessary to practice the disclosure in its broadest sense and are instead disclosed merely to particularly describe representative and preferred embodiments.

Various modifications to the embodiments may be apparent to one of skill in the art upon reading this disclosure. For example, persons of ordinary skill in the relevant arts will recognize that the various features described for the different embodiments can be suitably combined, un-combined, and re-combined with other features, alone, or in different combinations. Likewise, the various features described above should all be regarded as example embodiments, rather than limitations to the scope or spirit of the disclosure.

Persons of ordinary skill in the relevant arts will recognize that various embodiments can comprise fewer features than illustrated in any individual embodiment described above. The embodiments described herein are not meant to be an exhaustive presentation of the ways in which the various features may be combined. Accordingly, the embodiments are not mutually exclusive combinations of features; rather, the claims can comprise a combination of different individual features selected from different individual embodiments, as understood by persons of ordinary skill in the art.

Any incorporation by reference of documents above is limited such that no subject matter is incorporated that is contrary to the explicit disclosure herein. Unless indicated otherwise, references to "embodiment(s)", "disclosure", "present disclosure", "embodiment(s) of the disclosure", "disclosed embodiment(s)", and the like contained herein refer to the specification (text, including the claims, and figures) of this patent application that are not admitted prior art.

For purposes of interpreting the claims, it is expressly intended that the provisions of 35 U.S.C. 112(f) are not to be invoked unless the specific terms "means for" or "step for" are recited in the respective claim.

What is claimed is:

1. An endplate plunger assembly for anchoring a tether to opposed adjacent end plates of a spine, comprising:
   a sleeve defining an outer radial dimension at an open distal end;
   a shaft disposed within said sleeve, said shaft being translatable within said sleeve and including a distal end portion that is proximate said open distal end of said sleeve;
   a first resilient arm assembly affixed to said distal end portion of said shaft, said first resilient arm assembly including a proximal end portion and a distal end portion separated by a mid portion, said distal end portion of said first resilient arm assembly including a first tip portion that defines and extends along a first tip axis to a first distal extremity; and
   a second resilient arm assembly affixed to said distal end portion of said shaft, said second resilient arm assembly including a proximal end portion and a distal end portion separated by a mid portion, said distal end portion of said second resilient arm assembly including a second tip portion that defines and extends along a second tip axis to a second distal extremity,
   wherein:
   in a deployed configuration, said first tip axis is oriented to extend radially outward to said first distal extremity, said first distal extremity extending radially beyond said outer radial dimension of said sleeve in a first radial direction, and said second tip axis is oriented to extend radially outward to said second distal extremity, said second distal extremity extending radially beyond said outer radial dimension of said sleeve in a second radial direction, said second radial direction being opposite said first radial direction; and in a retracted configuration, said first resilient arm assembly and said second resilient arm assembly are elastically deformed to retract within said outer radial dimension of said sleeve.

2. The endplate plunger assembly of claim 1, wherein said sleeve defines an oblong cross-section.

3. The endplate plunger assembly of claim 1, wherein:
said mid portion of said first resilient arm assembly includes a first flexure;
said first tip portion defines a first notch;
said mid portion of said second resilient arm assembly includes a second flexure; and
said second tip portion defines a second notch.

4. The endplate plunger assembly of claim 3, wherein said first tip portion is a separate component attached to said first flexure and said second tip portion is a separate component attached to said second flexure.

5. The endplate plunger assembly of claim 3, wherein:
said first tip portion tapers to distal points on opposing sides of said first notch; and
said second tip portion tapers to distal points on opposing sides of said second notch.

6. The endplate plunger assembly of claim 3, wherein:
said first flexure defines and extends along a first termination axis at said distal end portion of said first resilient arm assembly;
said first tip portion extends at a first canted angle relative to said first termination axis;
said second flexure defines and extends along a second termination axis at said distal end portion of said second resilient arm assembly; and
said second tip portion extends at a second canted angle relative to said second termination axis.

7. The endplate plunger assembly of claim 6, wherein said first canted angle approximates an attack angle of said first tip portion and said second canted angle approximates an attack angle of said second tip portion.

8. The endplate plunger assembly of claim 1, wherein said distal end portion of said first resilient arm assembly and said distal end portion of said second resilient arm assembly each include a contact point that contacts an interior surface of said sleeve when in said retracted configuration.

9. The endplate plunger assembly of claim 1, wherein said mid portion of said first resilient arm assembly and said mid portion of said second resilient arm assembly are arcuate.

10. The endplate plunger assembly of claim 1, wherein:
said distal end portion of said first resilient arm assembly defines a first notch that is open to said first distal extremity of said distal end portion of said first resilient arm assembly, said first notch being configured for releasably mounting the tether thereto; and
said distal end portion of said second resilient arm assembly defines a second notch that is open to said second distal extremity of said distal end portion of said second resilient arm assembly, said second notch being configured for releasably mounting said tether thereto.

11. The endplate plunger assembly of claim 1, comprising a tether releasably coupled to said distal end portion of said first resilient arm assembly and to said distal end portion of said second resilient arm assembly.

12. The endplate plunger assembly of claim 11, wherein said tether includes opposing end portions separated by a mid portion, said opposing end portions being unitary with said mid portion.

13. The endplate plunger assembly of claim 12, wherein said opposing end portions include a coarse biocompatible material.

14. The endplate plunger assembly of claim 13, wherein said coarse biocompatible material is in the form of one of biocompatible metal, wire fragments, particulates, or hard tissue fragments.

15. The endplate plunger assembly of claim 12, wherein said opposing end portions are of a greater dimension than said mid-portion, said greater dimension being one of a thickness and a diameter.

16. The endplate plunger assembly of claim 15, wherein said tether is a flat ribbon, and said greater dimension is said thickness.

17. The endplate plunger assembly of claim 15, wherein said tether is a cord having a substantially circular cross-section, and said greater dimension is said diameter.

18. The endplate plunger assembly of claim 11, wherein said tether includes a growth-promoting material that promotes bone growth.

19. The endplate plunger assembly of claim 18, wherein said growth-promoting material is infused in a base material of said tether.

20. The endplate plunger assembly of claim 19, wherein said base material is one of a woven fabric tubing, a woven mesh, a non-woven mesh, a braided structure, and a woven structure.

* * * * *